US009359310B2

(12) United States Patent
Homman et al.

(10) Patent No.: US 9,359,310 B2
(45) Date of Patent: Jun. 7, 2016

(54) METHANETHIONE COMPOUNDS HAVING ANTIVIRAL ACTIVITY

(71) Applicants: Mohammed Homman, Nacka (SE); Ngarita Kingi, Alvsjo (SE); Jan Bergman, Spanga (SE); Robert Berg, Ronninge (SE)

(72) Inventors: Mohammed Homman, Nacka (SE); Ngarita Kingi, Alvsjo (SE); Jan Bergman, Spanga (SE); Robert Berg, Ronninge (SE)

(73) Assignee: VIRONOVA INFLUENZA AB, Stockholm (SE)

( * ) Notice: Subject to any disclaimer, the term of this patent is extended or adjusted under 35 U.S.C. 154(b) by 0 days.

(21) Appl. No.: 14/401,545

(22) PCT Filed: May 17, 2013

(86) PCT No.: PCT/EP2013/060266
§ 371 (c)(1),
(2) Date: Nov. 17, 2014

(87) PCT Pub. No.: WO2013/171334
PCT Pub. Date: Nov. 21, 2013

(65) Prior Publication Data
US 2015/0133468 A1    May 14, 2015

Related U.S. Application Data

(60) Provisional application No. 61/648,700, filed on May 18, 2012, provisional application No. 61/659,516, filed on Jun. 14, 2012, provisional application No. 61/666,286, filed on Jun. 29, 2012, provisional application No. 61/774,991, filed on Mar. 8, 2013.

(51) Int. Cl.
*C07D 295/16*    (2006.01)
*C07D 261/18*    (2006.01)
*C07D 249/10*    (2006.01)
*C07D 249/06*    (2006.01)

(52) U.S. Cl.
CPC ............ *C07D 261/18* (2013.01); *C07D 249/06* (2013.01); *C07D 249/10* (2013.01)

(58) Field of Classification Search
CPC ................................................... C07D 295/16
See application file for complete search history.

(56) References Cited

U.S. PATENT DOCUMENTS 8,207,205 B2    6/2012    Jones et al.

FOREIGN PATENT DOCUMENTS

| WO | 2004/078732 A1 | 9/2004 | |
| WO | WO 2004/078732 * | 9/2004 | ........... C07D 231/14 |
| WO | 2009-131957 | 10/2009 | |
| WO | 2011/015037 A1 | 2/2011 | |
| WO | 2012/044531 A1 | 4/2012 | |

OTHER PUBLICATIONS

Klingsberg et al., "Thiation with Phosphorus Pentasulfide in Pyridine Solution," Chemical Research Department, Schering Corporation, May 17, 1951.
International Search Report, dated Jun. 27, 2013, from corresponding PCT application.
Ching-Yao Su et al., "High-throughput identification of compounds targeting influenza RNA-dependent polymerase activity", Proceedings of the National Academy of Sciences, Nov. 9, 2010, pp. 19151-19156, vol. 107, No. 45.

* cited by examiner

*Primary Examiner* — Erich A Leeser
(74) *Attorney, Agent, or Firm* — Young & Thompson

(57) ABSTRACT

A compound of formula (I) is useful as an antiviral agent, in particular for the treatment of influenza. A method for preparing the compound of formula (I) and a composition including the compound of formula (I) are described.

29 Claims, 2 Drawing Sheets

METHANETHIONE COMPOUNDS HAVING ANTIVIRAL ACTIVITY

FIELD OF THE INVENTION

The present invention relates to thio derivatives having antiviral activity, in particular against influenza virus, to compositions comprising such compounds and to methods of preparing these derivatives and of using them.

The work leading to this invention has received funding from the European Union Seventh Framework Programme (FP7/2007-2013) under grant agreement no 259972.

BACKGROUND OF THE INVENTION

Influenza is caused by an RNA virus of the orthomyxoviridae family. Influenza viruses can be classified into three types (A, B and C), based on antigenic differences in the nucleoprotein and the matrix protein. Influenza A virus is very pathogenic for mammals (e.g. humans, pigs, ferrets, horses) and birds and causes a serious global health concern. Since 1900 over 50 million people have died from influenza.

International patent application No. PCT/CN2010/001187, published as WO 2011/015037, is directed to compounds which exhibit antiviral activity, particularly against influenza virus. In one embodiment, the compounds are heterocyclic amides containing piperazine and isoxazole rings and optionally substituted with one or more substituents. In one embodiment, the compounds described therein are represented by the formula

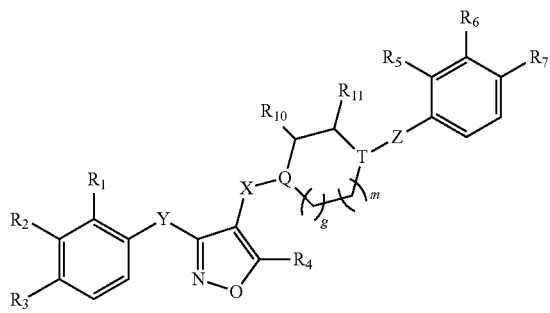

wherein X, Y, and Z are independently absent or selected from the group consisting of —C(=O)—, —S(=O)—, —SO$_2$—, —N(R$_{12}$)—, —C(R$_{13}$)=C(R$_{14}$)—, and —C(R$_{15}$R$_{16}$)$_n$—, n, g, and m are independently 0 to 6; Q and T are independently selected from nitrogen or CR$_{17}$; and R$_1$-R$_{17}$ are independently selected from hydrogen, halo, hydroxyl, linear or branched C$_1$-C$_6$ alkyl, linear or branched C$_1$-C$_6$ alkenyl, linear or branched C$_1$-C$_6$ alkynyl, or linear and branched C$_1$-C$_6$ alkoxy, amino, azido, cyano, nitro, nitrile, isonitrile, amide, carboxylate, urea, guanidine, isocyanate, isothiocyanate, and thioether.

International patent application No. PCT/US2011/052965, published as WO/2012/044531, discloses a compound of the formula:

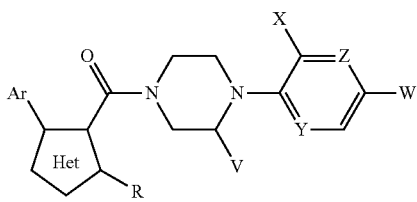

wherein Het is a 5 or 6-membered heterocycle with N, O, or S adjacent to the Ar substituent or adjacent to the point of attachment for the Ar substituent; Ar is aryl or heteroaryl; R is CH$_3$, CH$_2$F, CHF$_2$ or CH=CH$_2$; V is H, CH$_3$ or =O; W is NO$_2$, Cl, Br, CH$_2$OH, or CN; X is Cl, Br, F, CH$_3$, OCH$_3$, or CN; Y is CH or N; and Z is CH or N, useful in compositions for the prevention and treatment of influenza virus.

There still remains an urgent need for better treatment of viral infections, in particular infections by the influenza virus. Therefore, it is an object of the present invention to provide further antiviral compounds that effectively treat or prevent viral infections, particularly influenza infections, formulations containing these compounds, methods of making the compounds, and methods of using the compounds.

SUMMARY OF THE INVENTION

In a first aspect, a compound of formula (I) is provided:

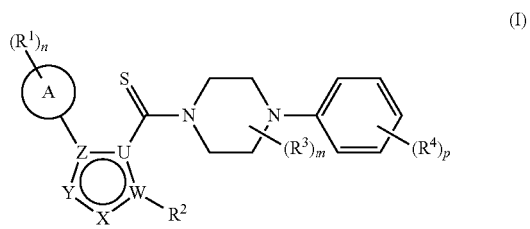

wherein
U is C or N;
W is C or N;
X is N, CH, O or NH;
Y is N, CH, O or NH;
Z is C or N;
the ring A

is 6-membered aryl or heteroaryl;
n is an integer of from 0 to 3;
m is an integer of from 0 to 2;
p is an integer of from 0 to 3;
each $R^1$ is independently selected from C1-C6 alkyl; C1-C6 alkoxy; OH; halogen; and $R^5R^6N$;
$R^2$ is selected from H and C1-C6 alkyl;
each $R^3$ is independently selected from C1-C6 alkyl;
each $R^4$ is independently selected from NO$_2$; halogen; C1-C6 alkyl and C1-C6 alkoxy;
$R^5$ and $R^6$ are independently selected from H and C1-C6 alkyl; wherein any alkyl is optionally substituted with one or several halogen atoms;
or a pharmaceutically acceptable salt thereof.

In another aspect, a compound of formula (I), as defined herein above, is provided for use in therapy, e.g. for use in the treatment of a viral infection, such as an infection by an influenza virus.

In still another aspect, a pharmaceutical composition is provided, comprising a compound as defined herein above, or a pharmaceutically acceptable salt thereof, and at least one pharmaceutically acceptable excipient.

In still another embodiment a pharmaceutical composition as defined herein above is provided for use in the treatment of a viral infection, such as an infection by an influenza virus.

In another aspect, a method is provided for preparing a compound of formula (I)

(I)

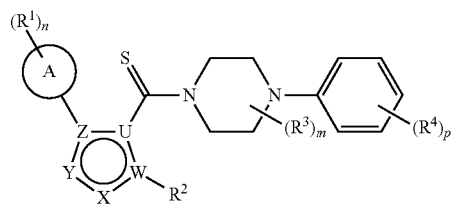

wherein
U is C or N;
W is C or N;
X is N, CH, O or NH;
Y is N, CH, O or NH;
Z is C or N;
the ring A

is 6-membered aryl or heteroaryl;
n is an integer of from 0 to 3;
m is an integer of from 0 to 2;
p is an integer of from 0 to 3;
each $R^1$ is independently selected from C1-C6 alkyl; C1-C6 alkoxy; OH; halogen; and $R^5R^6N$;
$R^2$ is selected from H and C1-C6 alkyl;
each $R^3$ is independently selected from C1-C6 alkyl;
each $R^4$ is independently selected from $NO_2$; halogen; C1-C6 alkyl and C1-C6 alkoxy;
each $R^5$ and $R^6$ is independently selected from H and C1-C6 alkyl;
wherein any alkyl is optionally substituted with one or several halogen atoms;
or a pharmaceutically acceptable salt thereof;
comprising reacting a compound of formula (II)

(II)

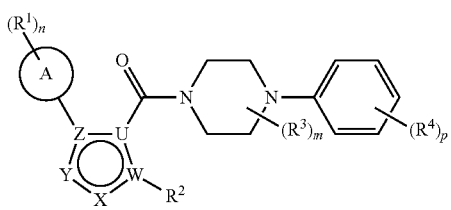

wherein X, Y, Z, U, W, the ring A, n, m, p, $R^1$, $R^2$, $R^3$ and $R^4$ are as defined herein above, with $P_2S_5.2C_5H_5N$ as a thionating agent, in a liquid solvent medium; and optionally preparing a pharmaceutically acceptable salt of the compound of formula (I).

DETAILED DESCRIPTION OF THE INVENTION

Unless otherwise indicated or apparent from the context, any alkyl group as referred to herein may be branched or unbranched. This also applies to said groups when present in moieties such as alkoxy groups.

The term "alkyl" as employed herein, alone or as part of another group, refers to an acyclic straight or branched alkyl chain radical, unless otherwise specified containing 1, 2, 3, 4, 5, or 6, carbons in the normal chain, which includes methyl, ethyl, n-propyl, n-butyl, n-pentyl, and n-hexyl. Examples of branched chain radicals, not excluding any of the possible isomers not mentioned, are iso-propyl, sec-butyl, tert-butyl, iso-pentyl, 3-methylpentyl, and the like. Unless otherwise indicated or apparent from the context, in the expression "any alkyl is optionally substituted with one or several halogen atoms", the reference to "any alkyl" includes alkyls which constitute either the radical per se, such as in $R^3$, or which are part of a functional group, e.g. an alkoxy radical.

Unless otherwise indicated or apparent from the context "any C1-C6 alkyl moiety" refers to an alkyl radical per se or an alkyl radical which is part of a functional group, e.g. an alkoxy radical.

The term "6-membered aryl" refers to phenyl.

The term "6-membered heteroaryl" refers to an aromatic ring containing 6 atoms in the ring, at least one of which, e.g. 1-3, or 1-2, e.g. 1, is a heteroatom, e.g. N. Examples of 6-membered hereroaryl are pyridyl, pyrimidyl, pyrazinyl, pyridazinyl and triazinyl.

The term "halogen" refers to fluoro, chloro, bromo and iodo, where the preferred halogen radicals are fluoro and chloro.

The term alkoxy refers to a radical of the type:

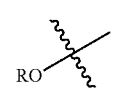

wherein R is an alkyl moiety.

The term nitro refers to the radical —$NO_2$.

The term influenza virus, as used herein, generally refers to a mammalian influenza virus, e.g.

a mammalian Influenza A virus, e.g., H3N2, H1N1, H2N2, H7N7 and H5N1 (avian influenza virus) strains and variants thereof.

In the compound of formula (I), the 5-membered ring containing X, Y, Z, U and W (the "5-ring") is a heteroaromatic ring which may be represented by formula (III)

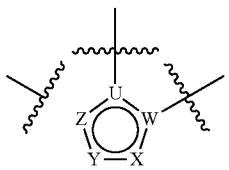

(III)

wherein

Figure 1:
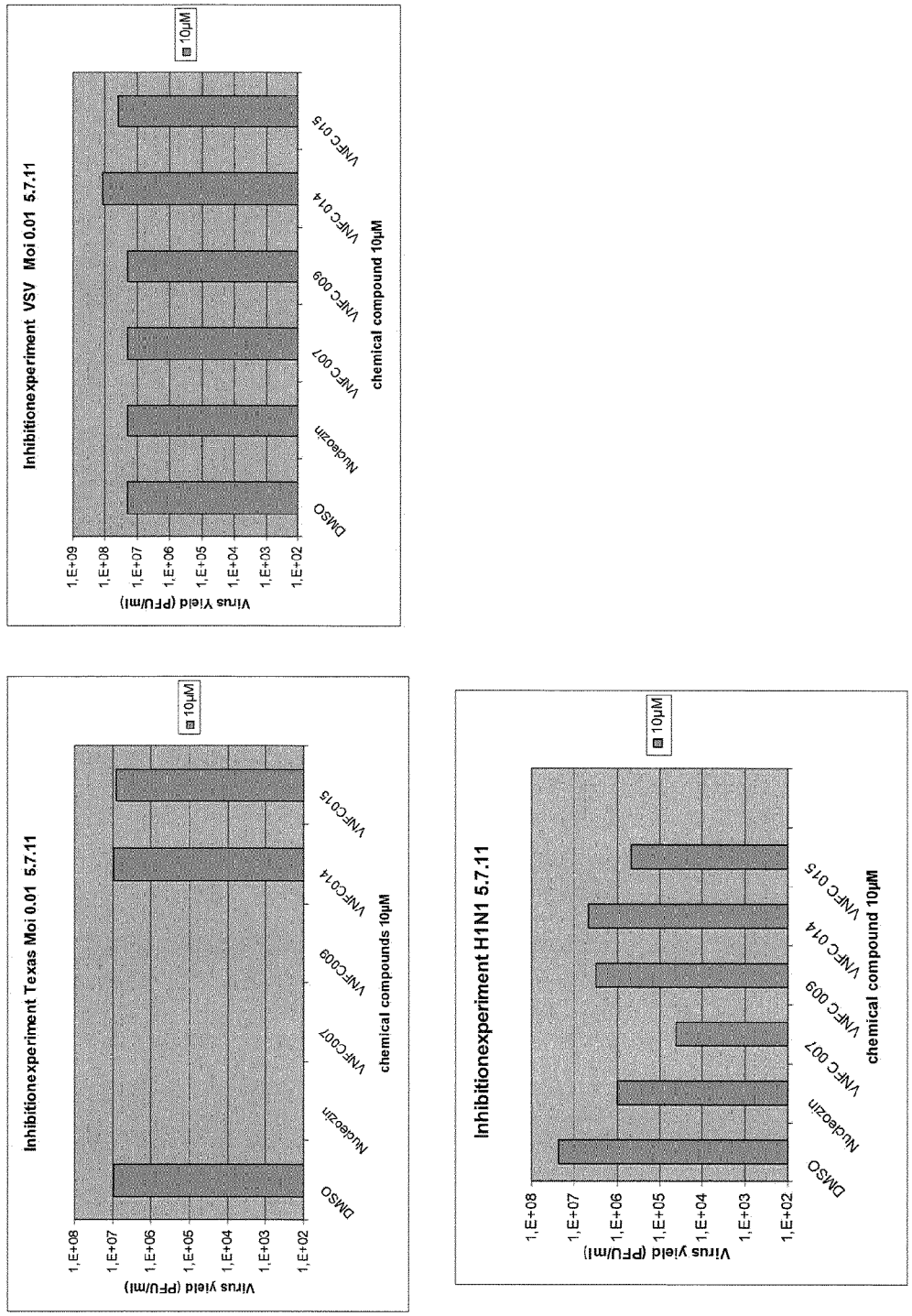
FIG. 1 is a bar chart diagram showing inhibition experiments performed on (A) Texas influenza virus, (B) H1N1 influenza virus and (C) Vesicular Stomatitis virus.

U is C or N;

W is C or N;

X is CH, N, NH or O;

Y is CH, N, NH or O; and

Z is C or N.

In some embodiments of a compound of formula (I), U is C. In other embodiments of a compound of formula (I), U is N.

In some embodiments of a compound of formula (I), W is C. In other embodiments of a compound of formula (I), W is N.

In some embodiments of a compound of formula (I), Z is C. In other embodiments of a compound of formula (I), Z is N.

For example, in some embodiments of a compound of formula (I), U is C, W is C, and Z is C or N; and in some other embodiments, U is C, W is C or N, and Z is C.

In still other embodiments, U, W and Z are all C.

In some embodiments of a compound of formula (I), X is N, NH or O; e.g. X is NH or O; or X is O. In some other embodiments, X is NH or N, e.g. X is N. In some embodiments, X is NH.

In some embodiments of a compound of formula (I), Y is N, NH or O; e.g. Y is NH or O; or Y is O. In some other embodiments, Y is NH or N, e.g. Y is N. In some embodiments, Y is NH.

A ring of formula (III) may correspond to any of the following alternatives:

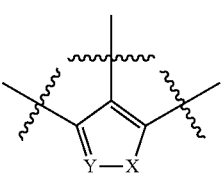

(IIIa)

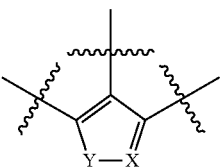

(IIIb)

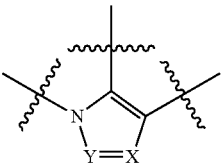

(IIIc)

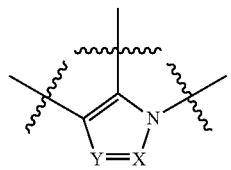

(IIId)

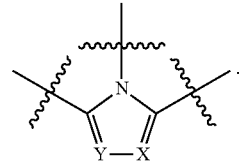

(IIIe)

When the 5-ring is a ring of formula (IIIa), X is NH or O; and Y is N or CH.

When the 5-ring is a ring of formula (IIIb), X is N or CH; and Y is NH or O.

When the 5-ring is a ring of formula (IIIc), X is N or CH; and Y is N or CH.

When the 5-ring is a ring of formula (IIId), X is N or CH; and Y is N or CH.

When the 5-ring is a ring of formula (IIIe), X is N or CH; and Y is N or CH.

In some embodiments, the 5-ring is a ring of formula (IIIa), and the compound of formula (I) may then be represented by formula (Ia)

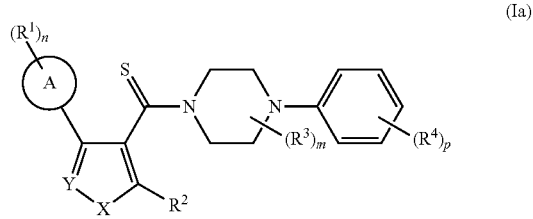

(Ia)

wherein X is NH or O; Y is N or CH; and n, m, p, the ring A, $R^1$, $R^2$, $R^3$ and $R^4$ are as defined herein above.

In some embodiments of a compound of formula (Ia), X is NH or O and Y is N; e.g. X is NH and Y is N; or X is O and Y is N.

In some embodiments, the 5-ring is a ring of formula (IIIb), and the compound of formula (I) may then be represented by formula (Ib)

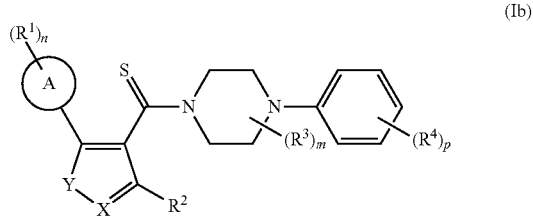

(Ib)

wherein X is N or CH; Y is NH or O; and n, m, p, the ring A, $R^1$, $R^2$, $R^3$ and $R^4$ are as defined herein.

In some embodiments of a compound of formula (Ib), X is N, and Y is NH or O; e.g. X is N and Y is NH; or X is N and Y is O.

In some embodiments, the 5-ring is a ring of formula (IIIc), and the compound of formula (I) may then be represented by formula (Ic)

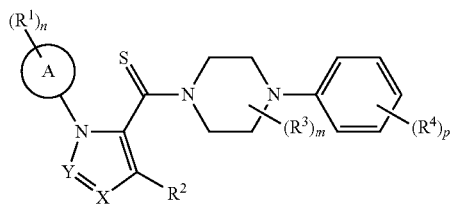

wherein X is N or CH; Y is N or CH; and n, m, p, the ring A, $R^1$, $R^2$, $R^3$ and $R^4$ are as defined herein above.

In some embodiments of a compound of formula (Ic), X is N, and Y is N or CH; e.g. X is N and Y is N; or X is N and Y is CH.

In some embodiments, the 5-ring is a ring of formula (IIId), and the compound of formula (I) may then be represented by formula (Id)

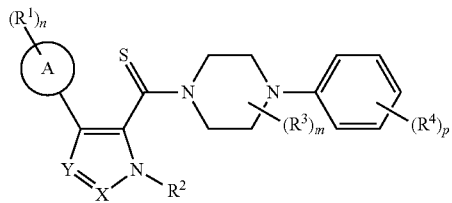

wherein X is N or CH; Y is N or CH; and n, m, p, the ring A, $R^1$, $R^2$, $R^3$ and $R^4$ are as defined herein above.

In some embodiments of a compound of formula (Id), X is N, and Y is N or CH; e.g. (X is N and Y is N; or X is N and Y is CH.

In some embodiments, the 5-ring is a ring of formula (IIIe), and the compound of formula (I) may then be represented by formula (Ie)

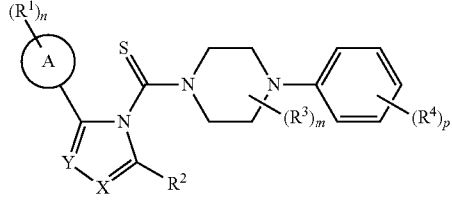

wherein X is N or CH; Y is N or CH; and n, m, p, the ring A, $R^1$, $R^2$, $R^3$ and $R^4$ are as defined herein above.

In some embodiments of a compound of formula (Ie), X is N, and Y is N or CH; e.g. X is N and Y is N; or X is N and Y is CH.

In some embodiments, the compound of formula (I) is a compound of formula (Ia), (Ib), (Ic) or (Id).

In some embodiments, the compound of formula (I) is a compound of formula (Ia) or (Ib).

In some embodiments, the compound of formula (I) is a compound of formula (Ic) or (Id).

In some embodiments, when the compound of formula (I) is a compound of formula (Ic) or (Id), both X and Y are N; and either W is C and Z is N; or W is N and Z is C, i.e. the compound is a triazole derivative of formula (Ic1)

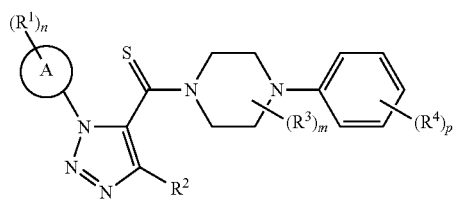

or formula (Id1)

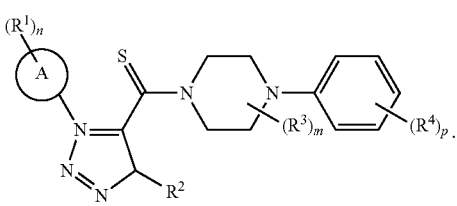

In the compound of formula (I), the ring A (herein below referred to simply as "A") is a 6-membered aromatic or heteroaromatic ring, i.e. A is phenyl or a 6-membered heteroaryl, e e.g. a 6-membered heteroaryl containing 1-3 N, such as 1 or 2 N, e.g. 1 N. In some embodiments, A is pyridyl, e.g. A is 3-pyridyl or 4-pyridyl. In some embodiments, A is phenyl, and the compound of formula (I) may then be represented by formula (If)

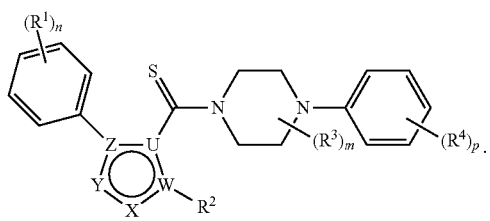

In some embodiments of a compound of formula (If), the five-membered ring is a triazole ring wherein X, Y and W are N and U and Z are C, and the compound may then be represented by formula (Id1f)

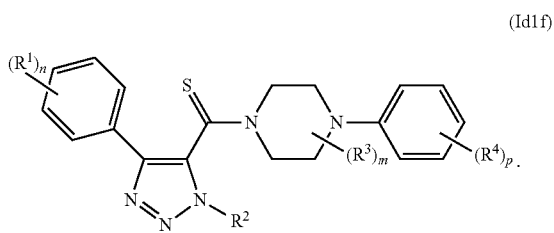

(Id1f)

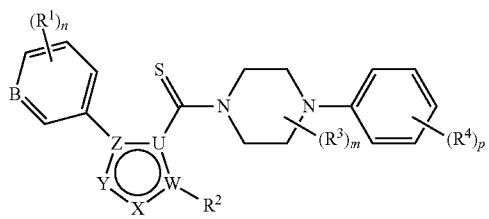

(Ig)

In some embodiments of a compound of formule (Id1f), $R^2$ is methyl.

In some embodiments of a compound of formula (I), A is phenyl having at least one substituent in ortho or para position, and the compound of formula (I) may then be represented by formula (If1)

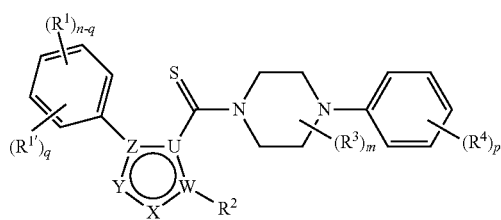

(If1)

wherein q is 1, 2 or 3; and each $R^{1'}$ is in ortho or para position on the phenyl ring.

In some embodiments of a compound of formula (If1), the five-membered ring is a triazole ring wherein X, Y and W are N and U and Z are C, and the compound may then be represented by formula (Id1f1)

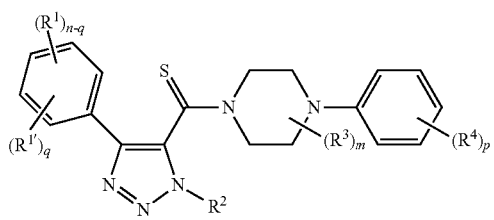

(Id1f1)

In some embodiments of a compound of formula (If1), e.g. in a compound of formula (Id1f1), each $R^{1'}$ is independently selected from C1-C6 alkoxy, OH and halogen, e.g. from C1-C3 alkoxy, OH and halogen, e.g. from methoxy, OH and halogen, such as methoxy, OH and F.

In some embodiments of a compound of formula (Id1f1), $R^2$ is methyl.

In some other embodiments, A is a 6-membered heteroaryl, e.g. a 6-membered heteroaryl containing 1-3 N, such as 1 or 2 N, e.g. 1 N. In some embodiments, A is pyridyl, e.g. A is 3-pyridyl or 4-pyridyl.

In some embodiments, A is phenyl or 3-pyridyl, and the compound of formula (I) may then be represented by formula (Ig)

wherein B is CH or N, e.g. B is N.

In formula (I), n is an integer of from 0 to 3, e.g. from 0 to 2, such as 0 or 1, e.g. 1;

m is an integer of from 0 to 2, e.g. 0 or 1, e.g. 0; and p is an integer of from 0 to 3, e.g. 1 or 2.

In some embodiments, n is an integer of from 0 to 2. In some other embodiments, n is 0 or 1. In some particular embodiments, n is 0.

In some embodiments, m is an integer of from 0 to 2. In some other embodiments, m is 0 or 1, e.g. 1. In some particular embodiments, m is 0.

In some embodiments, p is an integer of from 1 to 3. In some other embodiments, p is 1 or 2, e.g. 2. In some particular embodiments, p is 1.

For example, in some embodiments, both n and m are 0 or 1, e.g. both are 0, and p is an integer of from 1 to 3, e.g. 1 or 2.

In formula (I) each $R^1$ is independently selected from C1-C6 alkyl; C1-C6 alkoxy; OH; halogen; and $R^5R^6N$. In some embodiments, each $R^1$ is independently selected from C1-C6 alkyl; OH; halogen; and $R^5R^6N$. In some other embodiments, each $R^1$ is independently selected from C1-C6 alkyl and halogen, e.g. C1-C3 alkyl, fluoro and chloro, such as methyl, fluoro and chloro. In $R^5R^6N$, $R^5$ and $R^6$ are independently selected from H and C1-C6 alkyl, e.g. from H and C1-C3 alkyl, such as H and methyl, in particular H.

$R^2$ is selected from H and C1-C6 alkyl. In some embodiments, $R^2$ is selected from C1-C6 alkyl, e.g. C1-C3 alkyl, such as methyl. In some other embodiments, $R^2$ is selected from H and methyl.

Each $R^3$ is independently selected from C1-C6 alkyl. In some embodiments, each $R^3$ is independently selected from C1-C3 alkyl, e.g. each $R^3$ is methyl.

Each $R^4$ is independently selected from $NO_2$; halogen; C1-C6 alkyl and C1-C6 alkoxy. In some embodiments, each $R^4$ is independently selected from $NO_2$; halogen; and C1-C6 alkyl, e.g. from $NO_2$; halogen; and C1-C3 alkyl, or from $NO_2$; halogen; and C1-C3 alkyl, e.g. from $NO_2$; halogen; and methyl. When $R^4$ is halogen, it e.g. is Cl.

In some embodiments, the compound of formula (I) may be represented by formula (Ih)

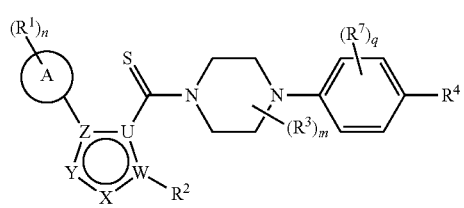

(Ih)

wherein the ring A, X, Y, Z, U, W, n, m, $R^1$, $R^2$, $R^3$ and $R^4$ are as defined herein above; q is an integer of from 0 to 2; and each $R^7$ is independently selected from $NO_2$; halogen; C1-C6 alkyl and C1-C6 alkoxy.

In some embodiments, each $R^7$ is independently selected from halogen; C1-C6 alkyl and C1-C6 alkoxy, such as halogen and C1-C6 alkyl, e.g. halogen. When $R^7$ is halogen, it e.g. is Cl.

In some embodiments, the integer q is selected from 0 and 1.

In some embodiments, in a compound of formula (I), in particular of formula (Ih), $R^4$ is selected from $NO_2$ and C1-C6 alkyl, e.g. $NO_2$ and C1-C3 alkyl; such as $NO_2$ and methyl; wherein any alkyl optionally is substituted with at least one halogen, e.g. at least one fluoro, such as in $CF_3$.

In some embodiments, in a compound of formula (Ih), $R^4$ is $NO_2$.

In some embodiments, in a compound of formula (Ih), q is 1, and $R^7$ is situated in ortho position on the phenyl ring, i.e. the compound may be represented by formula (Ij)

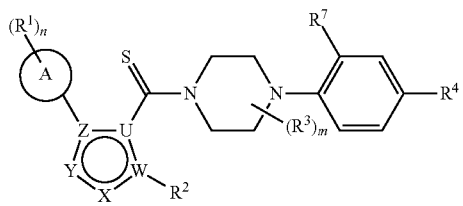
(Ij)

wherein A, X, Y, Z, U, W, n, m, $R^1$, $R^2$, $R^3$, $R^4$ and $R^7$ are as defined herein above.

In some other embodiments, in a compound of formula (Ih), q is 0, and the compound may then be represented by formula (Ik)

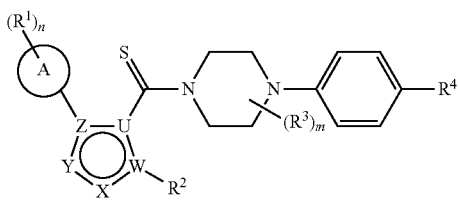
(Ik)

wherein A, X, Y, Z, U, W, n, m, $R^1$, $R^2$, $R^3$, and $R^4$ are as defined herein above.

In some embodiments of a compound of formula (Ik), $R^4$ is $CF_3$.

It should be understood that any reference to formula (I) also is meant as a reference to any one of the embodiments of said formula, as represented by formulas (Ia), (Ib), (Ic), (Id), (Ie), (If), (Ig), (Ih), (Ij) and (Ik), unless otherwise specified or clearly apparent from the context. Likewise, any combination of a particular embodiment as represented by (Ia), (Ib), (Ic), (Id) or (Ie), with a particular embodiment as represented by formula (If) or (Ig), and/or with a particular embodiment as represented by formula (Ih), (Ij) or (Ik) is contemplated within the scope of the invention.

For example, in some embodiments of a compound of formula (If), the compound is a compound of formula (Ij), i.e. the compound may be represented by formula (Ifj)

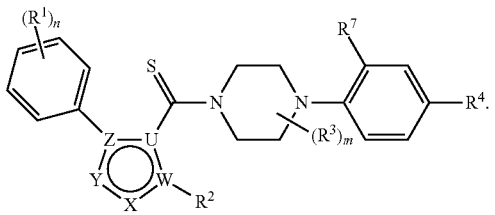
(Ifj)

In some embodiments of a compound of formula (Ifj), the compound is a compound of formula (Ia), i.e. the compound may be represented by formula (Iafj)

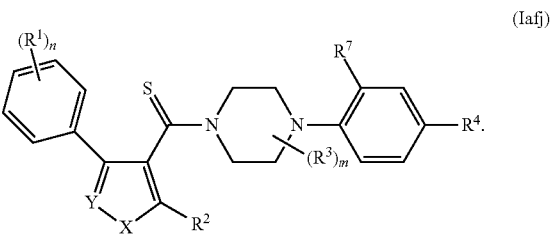
(Iafj)

In some other embodiments of a compound of formula (Ifj), the compound is a compound of formula (Id), i.e. the compound may be represented by formula (Idfj)

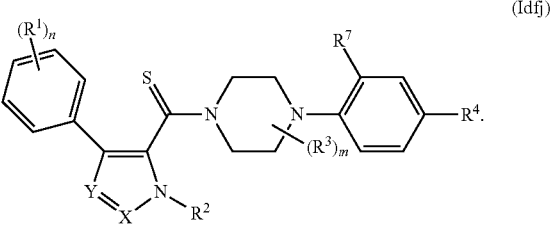
(Idfj)

Adopting a similar naming system, other particular embodiments are compounds of formula (Ibfj), (Icfj), (Iagj), (Iafk), (Iagk) etc.

Examples of compounds of the invention are

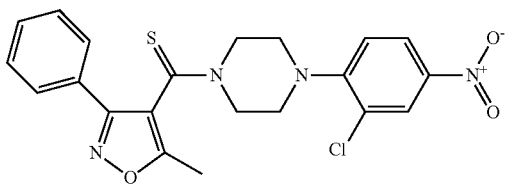 [SMILES: Cc1onc(-c2ccccc2)c1C(=S)N1CCN(c2ccc([N+](=O)[O-])cc2Cl)CC1]

(4-(2-chloro-4-nitrophenyl)piperazin-1-yl)(5-methyl-3-phenylisoxazol-4-yl)methanethione;

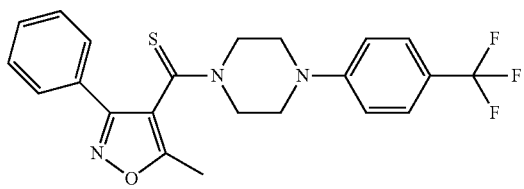 [SMILES: Cc1onc(-c2ccccc2)c1C(=S)N1CCN(c2ccc(C(F)(F)F)cc2)CC1]

(5-methyl-3-phenylisoxazol-4-yl)(4-(4-(trifluoromethyl)phenyl)piperazin-1-yl)methanethione;

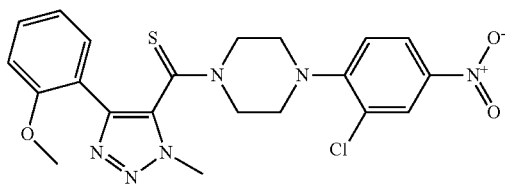 [SMILES: COc1ccccc1-c1nnn(C)c1C(=S)N1CCN(c2ccc([N+](=O)[O-])cc2Cl)CC1]

(4-(2-chloro-4-nitrophenyl)piperazin-1-yl)(4-(2-methoxyphenyl)-1-methyl-1H-1,2,3-triazol-5-yl)methanethione;

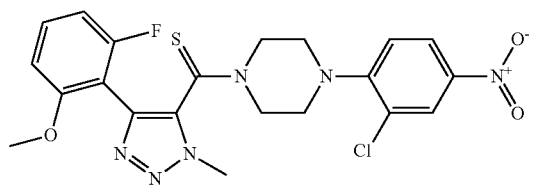 [SMILES: COc1cccc(F)c1-c1nnn(C)c1C(=S)N1CCN(c2ccc([N+](=O)[O-])cc2Cl)CC1]

(4-(2-chloro-4-nitrophenyl)piperazin-1-yl)(4-(2-fluoro-6-methoxyphenyl)-1-methyl-1H-1,2,3-triazol-5-yl)methanethione;

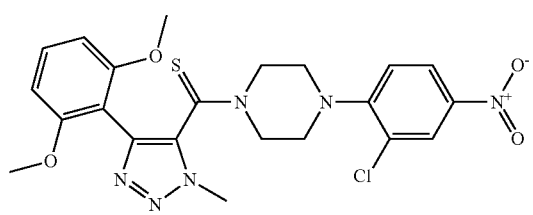 [SMILES: COc1cccc(OC)c1-c1nnn(C)c1C(=S)N1CCN(c2ccc([N+](=O)[O-])cc2Cl)CC1]

(4-(2-chloro-4-nitrophenyl)piperazin-1-yl)(4-(2,6-dimethoxyphenyl)-1-methyl-1H-1,2,3-triazol-5-yl)methanethione;

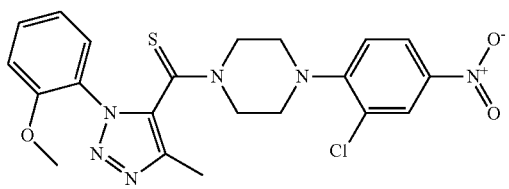 [SMILES: COc1ccccc1-n1nnc(C)c1C(=S)N1CCN(c2ccc([N+](=O)[O-])cc2Cl)CC1]

(4-(2-chloro-4-nitrophenyl)piperazin-1-yl)(1-(2-methoxyphenyl)-4-methyl-1H-1,2,3-triazol-5-yl)methanethione;

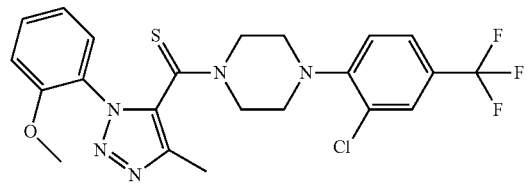

(4-(2-chloro-4-(trifluoromethyl)phenyl)piperazin-1-yl)(1-(2-methoxyphenyl)-4-methyl-1H-1,2,3-triazol-5-yl)methanethione;

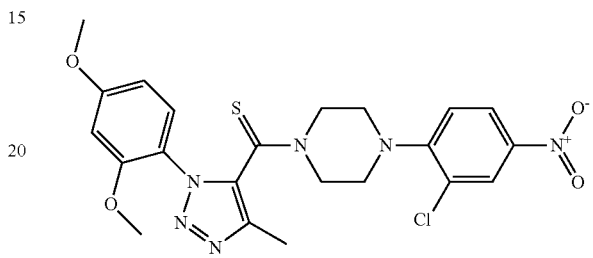

(4-(2-chloro-4-nitrophenyl)piperazin-1-yl)(1-(2,4-dimethoxyphenyl)-4-methyl-1H-1,2,3-triazol-5-yl)methanethione; and

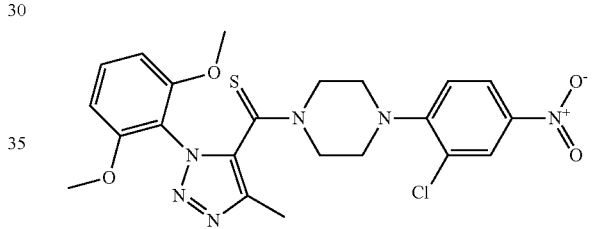

(4-(2-chloro-4-nitrophenyl)piperazin-1-yl)(1-(2,6-dimethoxyphenyl)-4-methyl-1H-1,2,3-triazol-5-yl)methanethione.

In some embodiments there is provided a pharmaceutically acceptable salt of the compound of formula (I). Examples of pharmaceutically acceptable salts for use in the pharmaceutical compositions of the present invention include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycolic, gluconic, succinic, and arylsulfonic acids.

"Pharmaceutically acceptable" as generally used herein refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The compound of formula (I) as described herein is useful for the prevention and treatment of viral infections, in particular influenza. In some embodiments, a compound of formula (I) is used to treat or prevent an influenza A viral infection. Influenza A viruses that can be prevented or treated with formulations and compounds as defined herein include H1N1, H2N2, H3N2, H5N1, H7N7, H1N2, H9N2, H7N2, H7N3, and H10N7. In some embodiments, the compound of formula (I) is useful for treatment of the influenza infection A strain caused by H1N1 or H3N2.

In one aspect, thus a pharmaceutical formulation is provided containing a compound of formula (I) and at least one pharmaceutically acceptable excipient. The pharmaceutically acceptable excipients that may be used in the invention, include, for example, vehicles, adjuvants, carriers or diluents, are well-known to those who are skilled in the art and are readily available to the public. The pharmaceutically acceptable carrier may be one that is chemically inert to the active compounds and that has no detrimental side effects or toxicity under the conditions of use. Pharmaceutical formulations are found e.g. in Remington's Pharmaceutical Sciences, 20th ed., Lippincott Williams & Wilkins, Baltimore, Md., 2000, p. 704.

The compounds of the formula (I) can be administered for any of the uses described herein by any suitable means, for example, orally, such as in the form of tablets or capsules, or parenterally, such as by e.g. intravenous injection or infusion techniques (e.g., as sterile injectable aqueous or non-aqueous solutions or suspensions). For a parenteral administration, a parenterally acceptable aqueous solution is employed, which is pyrogen free and has requisite pH, isotonicity and stability. Those skilled in the art are well able to prepare suitable solutions and numerous methods are described in the literature. A brief review of methods of drug delivery is also found in the scientific literature [e.g. Langer, Science 249:1527-1533 (1990)]. Also nasal or rectal administration is contemplated as possible.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The dose administered to a vertebrate subject, e.g. a mammal, particularly a human, in the context of the present invention should be sufficient to effect an antiviral therapeutic response in the mammal over a reasonable time frame. A person of ordinary skill in the art will recognize that dosage will depend upon a variety of factors including the potency of the specific compound, the age, condition and body weight of the patient, the nature and extent of the condition being treated, recommendations of the treating physician, and the therapeutics or combination of therapeutics selected for administration, as well as the stage and severity of the viral infection. The dose will also be determined by the route (administration form), timing and frequency of administration. In the case of oral administration the dosage can vary from about 0.01 mg to about 1000 mg per day of a compound of formula (I) or the corresponding amount of a pharmaceutically acceptable salt thereof.

The compounds of the present invention may be also be used or administered in combination with one or more additional therapeutically active ingredients, e.g. one or more substances useful in the treatment of viral infections or in alleviating symptoms associated with such infections, e.g. analgesics, antipyretics etc.

A compound of formula (I) may be prepared by reacting the corresponding oxo derivative of formula (II) with preferably crystalline 1,1'-[thiobis(mercaptophosphinothioylidene)]bis-,bis-pyridinium, e.g. using the thionating method as disclosed and claimed in the international patent application No. PCT/EP2012/051864, published as WO2012/104415, incorporated herein by reference, e.g. in a thionation reaction as represented in Reaction Scheme 1:

Reaction Scheme 1

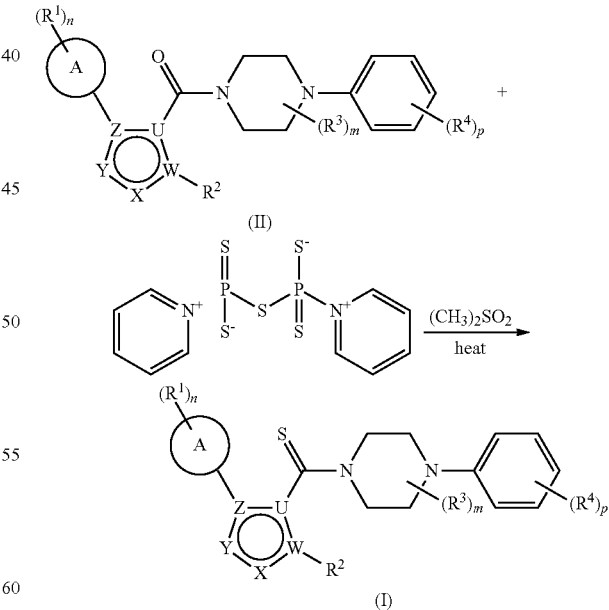

The synthesis of compounds of formula (II) is described e.g. in WO/2011/015037 and in WO/2012/044531, which documents are incorporated herein in their entirety by reference; see e.g. the general description at pages 39-42 and Examples 1-5 at pages 46-56 of WO 2011/015037; as well as pages 19-25 and Examples in WO/2012/044531. Further, a compound of formula (II) may be prepared by a method as represented in Reaction Scheme 2:

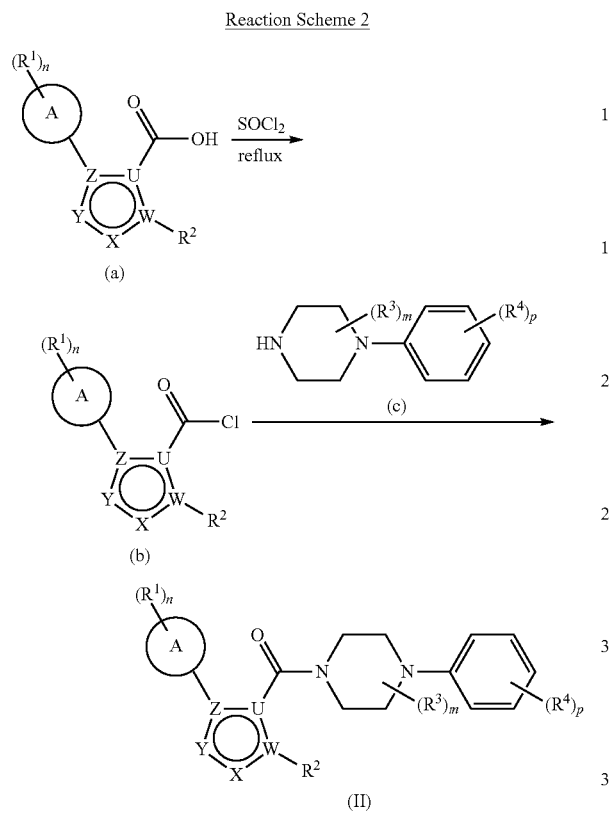

i.e. by reacting carboxylic acid derivative (a) with a chlorinating agent such as $SOCl_2$ so as to obtain carbonyl chloride derivative (b) and reacting (b) with substituted piperazine (c). The reaction components (a) and (c) are commercially available or may be prepared without undue difficulty, e.g. by following the general description in WO 2011/015037.

Also, in order to prepare a triazole derivative the starting material (a) in the reaction according to Reaction Scheme 2 may be prepared either by a reaction as described in U.S. Pat. No. 6,642,390 to Kolb et al., or in a method as described in Cheng, H. et al. J. Med Chem. 2012; 55; 2144-2153. Both documents are incorporated by reference herein in their entirety.

Also provided herein is a novel method for preparing a compound of formula (Id1f), wherein $R^2$ is methyl. As illustrated in Reaction Scheme 3, a compound of formula (a'), wherein $R^1$ and n is as defined with respect to formula (I), is prepared in a reaction comprising copper mediated cycloaddition of compound 1 with trimethylsilyl methylazide to give compound 2, which by removal of the TMS-group gives 3 exclusively. The carboxy group is introduced by lithiating 3 and quenching the lithiated 3 with carbon dioxide at low temperatures (−70° C.), giving the desired carboxylic acid (a').

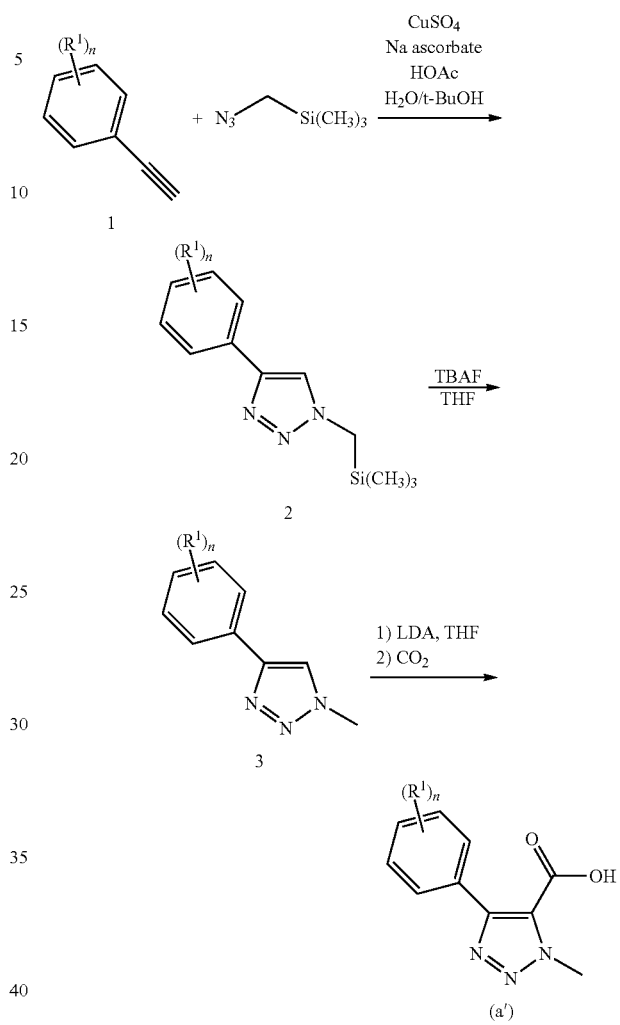

The compound (a') may then be further reacted as generally illustrated in Reaction Schemes 1 and 2 in order to provide a compound of formula (Id1f) wherein $R^2$ is methyl.

In some embodiments, the compound 1 in Reaction Scheme 3 is a compound 1'

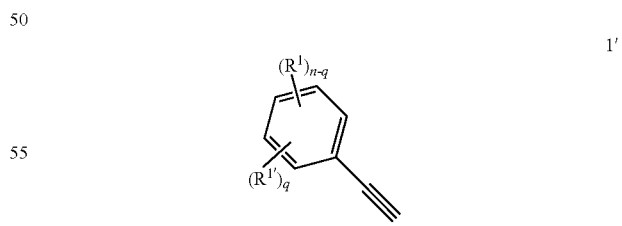

wherein n and $R^1$ are as defined with respect to formula (I), q is 1, 2 or 3 and each $R^{1'}$ is independently selected from C1-C6 alkoxy, OH and halogen, e.g. from C1-C3 alkoxy, OH and halogen, or from methoxy, OH and halogen, such as methoxy, OH and F; or wherein each $R^{1'}$ is independently selected from C1-C6 alkoxy, and halogen, e.g. from C1-C3 alkoxy, and halogen, or from methoxy, and halogen, such as methoxy and F.

Compound 1' may be prepared by a Negishi coupling reaction (Negishi, E-I.; Kotora, M.; Xu, C.; J. Org. Chem. 1997; 62; 8957-8960) of compound 4 using a zinc organic reagent of acetylene, as illustrated in Reaction Scheme 4. Alternatively, as also illustrated in Reaction Scheme 4, compound 1' may be prepared by a Sonogashira coupling reaction (Huang, Q.; Larock, R. C. J. Org. Chem. 2003; 68; 980-988) with ethynyl trimethylsilane giving compound 5, which is then reacted with tetra-n-butylammonium fluoride (TBAF) in THF to give compound F.

Reaction Scheme 4

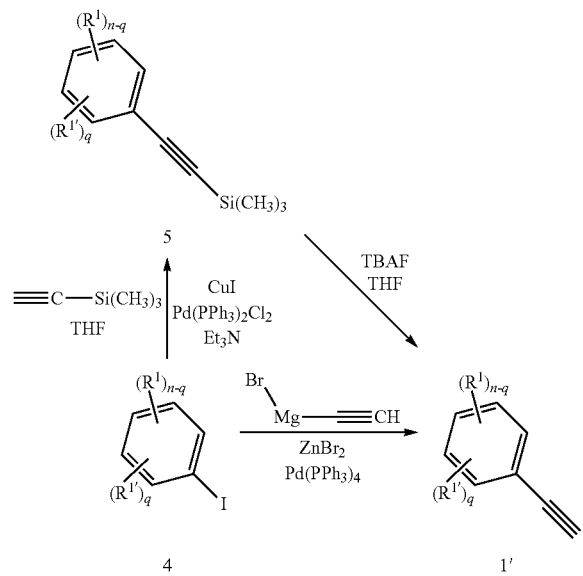

Various modifications may be made to the above illustrated methods, as will be apparent to a person of ordinary skill in the art.

EXAMPLES

The invention is illustrated in the following, non-limiting Examples.

Example 1

(4-(2-chloro-4-nitrophenyl)piperazin-1-yl)(5-methyl-3-phenylisoxazol-4-yl)methanethione

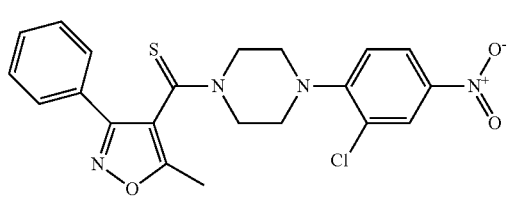 [SMILES: Cc1onc(-c2ccccc2)c1C(=S)N1CCN(c2ccc([N+](=O)[O-])cc2Cl)CC1]

1.1 Synthesis of 5-methyl-3-phenyl-isoxazole-4-carbonyl chloride

A mixture of 5-methyl-3-phenyl-isoxazole-4-carboxylic acid (1.0 g, 4.9 mmol, commercially available) and thionyl chloride (5 ml) was heated under reflux for 3 h. Removal of excess volatiles by evaporation afforded 5-methyl-3-phenyl-isoxazole-4-carbonyl chloride (1.01 g, 93%) as a yellow oil, which was used without further purification in the next reaction.

1.2 Synthesis of (4-(2-chloro-4-nitrophenyl)piperazin-1-yl)(5-methyl-3-phenylisoxazol-4-yl)methanone (nucleozin)

A solution of 5-methyl-3-isoxazole-4-carbonyl chloride (1.19 g, 5.37 mmol) in dioxane (15 ml, anhydrous) was added dropwise to a cooled mixture (0° C.) containing 1-(2-chloro-4-nitrophenyl)-piperazine (1.3 g, 5.37 mmol) and pyridine (0.81 ml, 0.01 mol) in dioxane (25 ml, anhydrous). The reaction solution was allowed to attain ambient temperature. Water was added to the solution affording an oily orange residue. The water was removed and the oily residue was dissolved in a mixture of MeOH/Acetonitrile (2:1) which gave crystalline nucleozin (1.74 g, 76%).

1.3 Synthesis of (4-(2-chloro-4-nitrophenyl)piperazin-1-yl)(5-methyl-3-phenylisoxazol-4-yl)methanethione A mixture of nucleozin (0.2 g, 0.47 mmol) and 1,1'-[thiobis(mercaptophosphinothioylidene)]-bis-,bis-pyridinium (0.38 g, 1 mmol) was heated for 10-15 minutes at 120° C. with dimethyl sulfone (1 g). Water was added to the melt and the reaction solution was allowed to boil for 10-15 minutes. After cooling, the precipitation was isolated by filtration affording crude material (0.2 g, 96%). Re-crystallization was achieved by dissolving in MeOH/Acetonitrile (2:1) and gave crystalline thionated nucleozin.

$^1$H-NMR (400 MHz, DMSO-d6) δ 8.21 (d, 1H, J=2.5 Hz), 8.14 (dd, 1H, J=9.0, 2.2 Hz), 7.64-7.63 (m, 2H), 7.53-7.52 (m, 2H), 7.15 (d, 1H, J=9.3 Hz), 4.50 (br, 1H), 4.35 (br, 1H), 3.69 (br, 1H), 3.50 (br, 1H), 3.39 (br, 1H), 3.18 (br, 1H), 3.08 (br, 1H), 2.48 (br, 1H), 2.47 (s, 3H).

$^{13}$C-NMR (400 MHz, DMSO-d6) δ 188.0 (s), 167.3 (s), 157.7 (s), 153.5 (s), 142.0 (s), 130.4 (d), 129.3 (d, 2C), 127.9 (s), 127.4 (d, 2C), 126.2 (s), 126.0 (d), 123.8 (d), 120.5 (d), 117.4 (s), 50.6 (t), 49.2 (t), 48.6 (t), 47.8 (t), 10.9 (q).

Example 2

(5-methyl-3-phenylisoxazol-4-yl)(4-(4-(trifluoromethyl)phenyl)piperazin-1-yl)methanethione

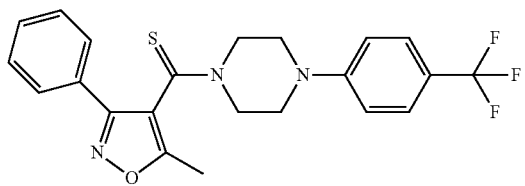

2.1 Synthesis of (5-methyl-3-phenyl-4-isoxazolyl)[4-[4-(trifluoromethyl)phenyl]-1-piperazinyl]-methanone A solution of 5-methyl-3-isoxazole-4-carbonyl chloride (1.19 g, 5.37 mmol) in dioxane (15 ml, anhydrous) was added dropwise to a cooled mixture (0° C.) containing 1-(4-trifluoro-methylphenyl)-piperazine (1.24 g, 5.38 mmol commercially available) and pyridine (0.81 ml, 0.01 mol) in dioxane (25 ml, anhydrous). The reaction solution was allowed to attain ambient temperature. Water was added to the solution affording a precipitation that was isolated by filtration. Recrystallization from a mixture of MeOH/Acetonitrile (2:1) afforded white crystalline compound (1.74 g, 75%).

$^1$H-NMR (400 MHz, DMSO-d6) δ 7.61-7.60 (m, 2H), 7.49-51 (m, 5H), 7.01-6.99 (m, 2H), 3.75 (br, 2H), 3.32 (br, 4H), 2.94 (br, 2H), 2.48 (s, 3H).

$^{13}$C-NMR (400 MHz, DMSO-d6) δ 169.6 (s), 162.4 (s), 160.5 (s), 153.6 (s), 131.0 (d), 129.8 (d, 2H), 129.1 (s), 128.2 (d, 2C), 127.0 (q, $^4J_{CF}$=3.7 Hz, CCF3, 2C), 125.8 (q, $^1J_{CF}$=270.1 Hz, CCF3), 119.6 (q, $^2J_{CF}$=32.0 Hz, CCF3), 115.4 (d, 2C), 112.0 (s), 48.0 (t, 4CH2), 12.1 (q).

2.2 Thionation of (5-methyl-3-phenyl-4-isoxazolyl)[4-[4-(trifluoromethyl)phenyl]-1-piperazinyl]-methanone A mixture of (5-methyl-3-phenyl-4-isoxazolyl)[4-[4-(trifluoromethyl)phenyl]-1-piperazinyl]-methanone (0.2 g, 0.48 mmol) and 1,1'-[thiobis(mercaptophosphinothioylidene)]bis-,bis Pyridinium (0.38 g, 1 mmol) was heated for 10-15 minutes at 120° C. with dimethyl sulfone (1 g). Water was added to the melt and the reaction solution was allowed to boil for 10-15 minutes. After cooling, the water was removed by filtration leaving a yellow precipitate (0.19 g, 92%). Recrystallization from a mixture of MeOH/Acetonitrile (2:1) afforded crystalline thionated (5-methyl-3-phenyl-4-isoxazolyl)[4-[4-(trifluoromethyl)phenyl]-1-piperazinyl]-methanone compound.

H-NMR (400 MHz, DMSO-d6) δ 7.63-7.62 (m, 2H), 7.47-52 (m, 5H), 7.00-6.94 (m, 2H), 4.5 (br, 1H), 4.20 (br, 1H), 3.63 (br, 2H), 3.47 (br, 1H), 3.27 (br, 2H), 2.54 (br, 1H), 2.45 (s, 3H).

$^{13}$C-NMR (400 MHz, DMSO-d6) δ 187.5 (s), 167.5 (s), 157.6 (s), 152.1 (s), 130.4 (d), 129.3 (d, 2C), 127.9 (s), 127.3 (d, 2C), 126.3 (q, $^4J_{CF}$=3.2 Hz, CCF3, 2C), 122.3 (q, $^1J_{CF}$=270.4 Hz, CCF3) 118.0 (q, $^2J_{CF}$=32.7 Hz, CCF3), 117.3 (s) 114.2 (d, 2C), 50.4 (t), 48.0 (t), 46.4 (t), 45.6 (t), 11.4 (q).

Example 3

General Procedure

Reaction Scheme 4

A mixture of the appropriately substituted iodobenzene 4 (1 eq), ethynyltrimethylsilane (1.2 eq), triethylamine (2.5 mL/1 g iodobenzene), THF (2.5 mL/1 g iodobenzene) was added to Pd(PPh$_3$)$_2$Cl$_2$ (0.025 eq) and CuI (0.1 eq) at room temperature under inert atmosphere. The reaction mixture was stirred for 3 days at room temperature. Saturated NH$_4$Cl (aq) (10 mL/1 g iodobenzene) was added to the reaction. The water solution was extracted with ethyl acetate (2×10 mL/1 g iodobenzene). The organic layer was washed with aqueous brine (10%), dried (Na$_2$SO$_4$) and filtered through a plug of SiO$_2$. The solvent was removed and the compound 5, in the form of an oil, was used directly in the next step.

TBAF (1.2 eq) in THF (1M) was added to a solution of 2-(trimethylsilyl)ethynyl-benzene derivative 5 (1 eq), water (2 eq) and THF (5 mL/1 g 2-(trimethylsilyl)ethynyl-benzene derivative 5) at 0° C. The reaction was allowed to attain room temperature. The reaction was stirred at room temperature until no starting material could be detected judging by TLC analysis (about 30 min). Aqueous brine (10%) solution (10 mL/1 g 2-(trimethylsilyl)ethynyl-benzene derivative 5) was added to the reaction. The aqueous phase was extracted with ethyl acetate (10 mL/1 g 2-(trimethylsilyl)ethynyl-benzene derivative 5×2). The combined organic phases were washed with aqueous brine (10%), dried (Na$_2$SO$_4$) and concentrated in vacuo and the dark oil was purified by chromatography using ethyl acetate and petroleum ether (60-80° C.) to give compound 1'.

Example 4

General Procedure

Reaction Scheme 4

A solution of ZnBr$_2$ in THF (25 mL) was added to a solution of ethynylmagnesium bromide in THF (0.5M, 75 mL) under argon at room temperature. The mixture was stirred for a further 1.5 h under argon before the addition of compound 4 (1 eq). A solution of Pd(PPh$_3$)$_4$ (0.05 eq) was added to the slurry and the reaction was stirred for a further 17 h at room temperature. NH$_4$Cl was added to the reaction mixture and the phases were separated. The water phase was extracted with ethyl ether (2×40 mL) dried with Na$_2$SO$_4$. The solvent was removed by evaporation under reduced pressure. Chromatography with SiO$_2$ and (1:9) Ethyl acetate/petroleum ether followed by a second chromatography with ethyl acetate/petroleum ether (0:1 then gradually 2% ethyl acetate in petroleum ether) gave compound 1'.

Examples of compounds 1' prepared by following either of Example 3 and Example 4 are:

1-fluoro-3-methoxy-2-ethynylbenzene

IR νmax: 3265, 3021, 2842, 1608, 1472, 1242, 774, 721 cm-1; δH (CDCl3): 7.28 (1H, td), 6.74 (2H, m), 3.94 (3H, s), 3.55 (1H, s); and 1-methoxy-2-ethynylbenzene IR νmax: 3285, 2943, 2836, 1595, 1489, 1249, 748 cm-1; δH (CDCl3): 7.49 (1H, dd), 7.34 (1H, dt), 6.93 (2H, m), 3.93 (3H, s), 3.33 (1H, s).

Example 5

General Procedure

Reaction Scheme 3

Trimethylsilyl methylazide (2 eq) and a solution of acetic acid (0.3 eq), water (5 mL/1 g compound 1) and t-butanol (10 mL/1 g compound 1) were added to compound 1 (1 eq), copper sulfate (0.05 eq) and sodium ascorbate (0.15 eq). The reaction was heated at 50° C. until no remaining compound 1 could be detected judging by TLC analysis (about 1-2 h). The reaction mixture was cooled to room temperature. The water solution was extracted with diethyl ether (20 mL/1 g compound ×2). The combined ether phases were washed with aqueous brine (10%), dried (Na$_2$SO$_4$) and concentrated in vacuo and the dark oil was purified by chromatography using ethyl acetate and petroleum ether (60-80° C.), to give compound 2.

TBAF (1.2 eq) in THF (1M) was added to a solution of 2 (1 eq), water (2 eq) and THF (5 mL/1 g 2) at 0° C. The reaction was allowed to attain room temperature. The reaction was stirred at room temperature until no starting material could be detected judging by TLC analysis (about 30 min). Aqueous brine (10%) solution (10 mL/1 g of 2) was added to the reaction. The water phase was extracted with ethyl acetate (10 mL/1 g of 2×2). The combined organic phases were washed with aqueous brine (10%), dried ($Na_2SO_4$) and concentrated in vacuo and the dark oil was purified by chromatography using ethyl acetate and petroleum ether (60-80° C.), giving 3.

A solution of LDA (2M) in THF (1.25 eq) was added to a solution of 3 in THF under argon at −75° C. for 20 min. The slurry was stirred at −75° C. for 1 h. Carbon dioxide was bubbled through the solution for 10 min at −75° C. and the reaction mixture thereafter was allowed to attain room temperature while keeping carbon dioxide bubbling through the reaction mixture. Water (15 mL/1 g of 3) was added. The THF was removed by evaporation under reduced pressure. The aqueous solution was washed with ethyl acetate (15 mL/1 g of 3×2). The water phase was acidified with hydrochloric acid (36%) and after a couple of minutes stirring a solid was formed. The solid was isolated by filtration and washed with water (5 mL/1 g of 3×3) and dried, giving compound a'.

Example of an intermediary compound 2 prepared in the general procedure of Example 5 is: 1-[(trimethylsilyl)methyl]-4-(6-fluoro-2-methoxyphenyl)-[1,2,3]triazole Yield: 75% (Yellow oil). IR νmax: 2955, 2840, 1581, 1476, 1231, 844, 781 cm-1; δH (CDCl3): 7.74 (1H, s), 7.28 (1H, td), 6.81 (2H, m), 3.99 (2H, s), 3.90 (3H, s), 0.20 (9H, s).

Examples of compounds a' prepared by following the general procedure of Example 5 are: 1-methyl-4-(2-methoxyphenyl)-[1,2,3]triazole-5-carboxylic acid Yield: 83% (White solid). Mp: 178° C.; IR νmax: 1701, 1459, 1246, 1170, 1023, 769, 747, 731 cm-1; δH (CDCl3): 7.42 (1H, dd), 7.29 (1H, m), 6.94 (1H, m), 6.86 (1H, d), 4.23 (3H, s), 3.69 (3H, s); and 1-methyl-4-(2,6-dimethoxyphenyl)-[1,2,3]triazole-5-carboxylic acid Yield: 48% (White solid). Mp: 205° C.; IR νmax: 1704, 1610, 1472, 1251, 1107, 775, 739, 717 cm-1; δH (CDCl3): 7.20 (1H, t), 6.50 (2H, d), 4.22 (3H, s), 3.61 (6H, s); δC:

Example 6

General Procedure

Reaction Scheme 2

A mixture of the carboxylic acid a (1 eq) and thionyl chloride (10 eq) was heated at reflux for 5 h. Toluene (3×20 mL/g carboxylic acid) was added to the reaction and the solvent was removed by evaporation under reduced pressure. The in situ formed acid chloride b was dissolved in dichloromethane (10 mL/g carboxylic acid). The solution was added slowly to a mixture of the piperazine c (1.2 eq), triethylamine (3 eq) and dichloromethane (10 mL/g carboxylic acid) at room temperature. The reaction was stirred at room temperature for 12-24 h. The reaction mixture was washed with water, sodium hydroxide solution (1M), and aqueous brine solution (10%), dried ($Na_2SO_4$) and concentrated in vacuo and the solid was purified by chromatography using ethyl acetate and petroleum ether (60-80° C.) or methanol and dichloromethane, giving the compound of formula (II).

Examples of compounds of formula (II) prepared by following the general procedure of Example 6 are:

(4-(2-chloro-4-nitrophenyl)piperazin-1-yl)(4-(2-methoxyphenyl)-1-methyl-1H-1,2,3-triazol-5-yl)methanone (VNFC 040)

Yield: 99% (Yellow solid). Mp: 126° C.; IR νmax: 1652, 1515, 1340, 1231, 1019, 755, 703 cm-1; δH (CDCl3): 8.25 (1H, d), 8.10 (1H, dd), 7.83 (1H, dd), 7.43 (1H, m), 7.13 (1H, t), 7.00 (1H, m), 6.85 (1H, d), 4.20 (3H, s), 3.94 (2H, m), 3.82 (3H, s), 3.24 (2H, m), 3.15 (2H, m), 2.55 (2H, br s), 1.76 (2H, br s);

(4-(2-chloro-4-nitrophenyl)piperazin-1-yl)(4-(2-fluoro-6-methoxyphenyl)-1-methyl-1H-1,2,3-triazol-5-yl)methanone (VNFC 050)

Yield: 90% (Yellow solid). Mp: 148° C.; IR νmax: 1650, 1513, 1471, 1340, 1232, 1080, 1020, 786, 766, 744, 704 cm-1; δH (DMSO-d6): 8.23 (1H, d), 8.15 (1H, dd), 7.51 (1H, td), 7.10 (1H, d), 7.00 (2H, m), 4.12 (3H, s), 3.74 (3H, s), 3.70 (2H, m), 3.18 (2H, m), 3.08 (2H, m), 2.54 (2H, m);

(4-(2-chloro-4-nitrophenyl)piperazin-1-yl)(4-(2,6-dimethoxyphenyl)-1-methyl-1H-1,2,3-triazol-5-yl)methanone (VNFC 044)

Yield: 84% (Yellow solid). Mp: 188° C.; IR νmax: 1642, 1582, 1473, 1331, 1255, 1107, 1014, 785, 761 cm-1; δH (CDCl3): 8.25 (1H, d), 8.10 (1H, dd), 7.39 (1H, t), 6.78 (1H, d), 6.68 (1H, d), 4.23 (3H, s), 3.80 (8H, m), 3.33 (2H, m), 3.0 (2H, m), 2.25 (2H, m);

(4-(2-chloro-4-nitrophenyl)piperazin-1-yl)(1-(2-methoxyphenyl)-4-methyl-1H-1,2,3-triazol-5-yl)methanone (VNFC 025)

Yield: 74% (Yellow solid). Mp: 186° C.; IR νmax: 1636, 1506, 1450, 1333, 1227, 1015, 763, 747 704 cm-1; δH (CDCl3): 8.28 (1H, d), 8.13 (1H, dd), 7.55 (1H, dd), 7.50 (1H, m), 7.15 (1H, m), 7.08 (1H, d), 7.00 (1H, d), 3.87 (5H, br s), 3.49 (2H, m), 3.15 (2H, m), 2.95 (2H, m), 2.50 (3H, s);

(4-(2-chloro-4-(trifluoromethyl)phenyl)piperazin-1-yl)(1-(2-methoxyphenyl)-4-methyl-1H-1,2,3-triazol-5-yl)methanone (VNFC 042)

Yield: 82% (White solid). Mp: 166° C.; IR νmax: 1650, 1504, 1446, 1325, 1268, 1107, 1019, 820, 749, 698 cm-1; δH (CDCl3): 7.65 (1H, d), 7.56 (1H, dd), 7.50 (2H, m), 7.15 (1H, t), 7.08 (1H, d), 7.01 (1H, d), 3.84 (5H, br s), 3.49 (2H, m), 3.07 (2H, m), 2.95 (2H, m), 2.51 (3H, s);

(4-(2-chloro-4-nitrophenyl)piperazin-1-yl)(1-(2,4-dimethoxyphenyl)-4-methyl-1H-1,2,3-triazol-5-yl)methanone (VNFC 027)

Yield: 58% (Yellow solid). Mp: 115° C.; IR νmax: 2926, 2852, 1643, 1510, 1336, 1209, 1011, 886, 789, 770, 746, 694 cm-1; δH (CDCl3): 8.30 (1H, d), 8.14 (1H, dd), 7.57 (1H, s), 7.04 (1H, d), 6.61 (1H, s), 3.99 (3H, s), 3.85 (5H, m), 3.60 (2H, m), 3.21 (2H, m), 3.13 (2H, m), 2.48 (3H, s); and (4-(2-chloro-4-nitrophenyl)piperazin-1-yl)(1-(2,6-dimethoxyphenyl)-4-methyl-1H-1,2,3-triazol-5-yl)methanone (VNFC 047)

Yield: 72% (Yellow solid). Mp: 188° C.; IR νmax: 2931, 2834, 1649, 1509, 1441, 1336, 1224, 1133, 1041, 1011, 881, 823, 774, 747, 705 cm-1; δH (CDCl3): 8.28 (1H, d), 8.12 (1H, dd), 7.14 (1H, d), 7.02 (3H, m), 3.82 (5H, m), 3.77 (3H, s), 3.54 (2H, m), 3.19 (2H, m), 3.05 (2H, m), 2.49 (3H, s).

Example 7

General Procedure

Reaction Scheme 1

Diphosphorus pentasulfide dipyridinium complex (3 eq) was added to a solution of a compound of formula (II) in dimethyl sulfone (4 g/g of compound of formula (II)) at 120-145° C. When the TLC analysis showed no starting material left the melt was cooled to room temperature. Water (40 mL/g of compound of formula (II)) was added and the mixture was heated at reflux for 5-10 min. The solid thus formed was isolated by filtration and washed with water. The crude product was purified by chromatography using ethyl acetate and petroleum ether (60-80° C.) or methanol and dichloromethane and recrystallized giving a compound of formula (I).

Examples of compounds of formula (I) prepared by following the general procedure of Example 7 are:

(4-(2-chloro-4-nitrophenyl)piperazin-1-yl)(4-(2-methoxyphenyl)-1-methyl-1H-1,2,3-triazol-5-yl)methanethione (VNFC 041)

Yield: 78% (Orange solid). Mp: 188° C.; IR $v_{max}$: 1583, 1474, 1433, 1336, 1227, 1013, 827, 755, 743, 698 cm⁻; $δ_H$ (CDCl₃): 8.26 (1H, d), 8.10 (1H, dd), 7.72 (1H, dd), 7.43 (1H, td), 7.10 (1H, t), 6.98 (1H, d), 6.82 (1H, d), 4.70 (1H, m), 4.24 (4H, m), 3.80 (3H, s), 3.50 (2H, m), 3.42 (1H, m), 2.99 (1H, m), 2.81 (1H, m), 2.12 (1H, m).

(4-(2-chloro-4-nitrophenyl)piperazin-1-yl)(4-(2-fluoro-6-methoxyphenyl)-1-methyl-1H-1,2,3-triazol-5-yl)methanethione (VNFC 051)

Yield: 53% (Orange solid). Mp: 213° C.; IR $v_{max}$: 1623, 1582, 1434, 1336, 1228, 1978, 1014, 784, 743, 698 cm⁻¹; $δ_H$: 8.27 (1H, d), 8.11 (1H, dd), 7.39 (1H, td), 6.83 (3H, m), 4.70 (1H, m), 4.23 (3H, s), 3.78 (3H, s), 3.60 (2H, m), 3.39 (1H, m), 2.98 (2H, m), 2.26 (1H, m).

(4-(2-chloro-4-nitrophenyl)piperazin-1-yl)(4-(2,6-dimethoxyphenyl)-1-methyl-1H-1,2,3-triazol-5-yl)methanethione (VNFC 045)

Yield: 39% (Orange solid). Mp: 230° C.; IR $v_{max}$: 1583, 1471, 1327, 1226, 1103, 1009, 790, 769, 743, 681 cm⁻¹; $δ_H$ (CDCl₃): 8.27 (1H, d), 8.11 (1H, dd), 7.38 (1H, t), 6.79 (1H, d), 6.66 (2H, m), 4.86 (1H, m), 4.28 (3H, s), 3.92 (1H, m), 3.75 (7H, m), 3.46 (2H, m), 2.87 (1H, m), 2.74 (1H, m), 1.89 (1H, m).

(4-(2-chloro-4-nitrophenyl)piperazin-1-yl)(1-(2-methoxyphenyl)-4-methyl-1H-1,2,3-triazol-5-yl)methanethione (VNFC 026)

Yield: 16% (Yellow solid) Mp: IR $v_{max}$: cm⁻¹; $δ_H$ (CDCl₃): 8.30 (1H, s), 8.15 (1H, dd), 7.52 (2H, m), 7.14 (1H, td), 7.07 (1H, d), 6.99 (1H, m), 4.48 (1H, m), 4.30 (1H, m), 3.80 (4H, m), 3.59 (1H, m), 3.25 (1H, m), 3.16 (2H, m), 2.85 (1H, m), 2.48 (3H, s).

(4-(2-chloro-4-(trifluoromethyl)phenyl)piperazin-1-yl)(1-(2-methoxyphenyl)-4-methyl-1H-1,2,3-triazol-5-yl)methanethione (VNFC 043)

Yield: 83% (Yellow solid). Mp: 163° C.; IR $v_{max}$: cm⁻¹; $δ_H$ (CDCl₃): 7.66 (1H, d), 7.51 (3H, m), 7.12 (1H, td) 7.07 (1H, d), 7.00 (1H, d), 4.46 (1H, m), 4.31 (1H, m), 3.82 (3H, s), 3.78 (1H, m), 3.58 (1H, m), 3.17 (1H, m), 3.07 (2H, m), 2.75 (1H, m), 2.46 (1H, s).

(4-(2-chloro-4-nitrophenyl)piperazin-1-yl)(1-(2,4-dimethoxyphenyl)-4-methyl-1H-1,2,3-triazol-5-yl)methanethione (VNFC 028)

Yield: 50% (Yellow solid). Mp: 199° C.; IR $v_{max}$: 1584, 1512, 1490, 1337, 1229, 1210, 1020, 818, 769, 746, 712 cm⁻¹; $δ_H$ (CDCl₃): 8.31 (1H, d), 8.15 (1H, dd), 7.52 (1H, s), 7.04 (1H, d), 6.59 (1H, s), 4.63 (1H, m), 4.25 (1H, m), 3.98 (3H, s), 3.82 (3H, s), 3.62 (1H, m), 3.30 (3H, m), 3.08 (1H, m), 2.43 (3H, s).

(4-(2-chloro-4-nitrophenyl)piperazin-1-yl)(1-(2,6-dimethoxyphenyl)-4-methyl-1H-1,2,3-triazol-5-yl)methanethione (VNFC 046)

Yield: 62% (Orange solid). Mp: 195° C.; IR $v_{max}$: 1582, 1508, 1479, 1335, 1225, 1018, 802, 746, 705 cm⁻¹; $δ_H$ (CDCl₃): 8.31 (1H, d), 8.15 (1H, dd), 7.12 (1H, d), 7.01 (3H, m), 4.50 (1H, m), 4.34 (1H, m), 3.78 (7H, m), 3.63 (1H, m), 3.22 (3H, m), 2.90 (1H, m), 2.45 (3H, s).

Biological Tests
Materials and Methods
MDCK cells in 24-well plates prepared a day earlier to reach ca. 80% cell confluence before virus infection
DMEM (Invitrogen) containing Pen/Step and 10% fetal bovine serum
OptiMEM with 0.3% BSA (Invitrogen)
PBS without supplements
Trypsin 1 μg/μl
VSV serotype Indiana in DMEM containing 0.1% BSA
Influenza A/Texas/91 (H1N1) in DMEM containing 0.1% BSA Viral Reduction Assay
Inhibition effect of the compounds was determined on Mardin-Darby canine kidney (MDCK) cells using viral reduction assay (VRA). One day prior to infection, MDCK cells seeded in 24-well cell culture plates were grown to 80% confluence in DMEM medium containing 10% fetal bovine serum, glutamine and Pen/Step at 37° C. in 5% $CO_2$. Prior to infection, the medium was removed and the cells were washed once with PBS. Virus stocks were diluted in serum-free minimal essential medium (OptiMEM, Invitrogen) containing 0.3% BSA immediately before use. Infection was performed in a volume of 200 μl per well at a multiplicity of infection (MOI) of 0.01 at room temperature for 1 h. The cells were then washed once with PBS and fresh DMEM medium containing 0.1% BSA and 10 μM of compounds was added to the cells. In the case of influenza A virus, the medium further contained 0.5 μg/ml of trypsin. The medium from infected wells were collected after 24 h and stored at −80° C. until assessed for viral replication.

Analysis of Virus Replication
MDCK cells in 12-well plates prepared a day earlier to reach ca. 80% cell confluence before virus infection
OptiMEM containing 0.3% BSA (Invitrogen)
Avicel MEDIUM (with trypsin)
12 ml required for each plate:
12 ml DMEM 2× (penicillin-streptomycin)
12 μl trypsin (μg/μl)
12 ml avicel (3% in $H_2O$)

Mix immediately before use

4% formaldehyde in PBS 0.5% crystal violet in 20% EtOH/water

Viral titers were assessed by plaque assay on MDCK cells. 10-fold serial dilutions of the virus preparations (from $10^{-2}$ to $10^{-7}$, 500 µl volume each) were prepared in OptiMEM containing 0.3% BSA. The cells were washed once with PBS, before the virus dilutions (500 µl) were added and the cells incubated for 1 h at room temperature. Then, the inoculum was removed and replaced with 2 ml Avicel medium before the plates were incubated for 72 h at 37° C. in 5% $CO_2$. For VSV titration, trypsin-free Avicel medium was used. To visualize virus plaques, the Avicel medium was removed, and the cells were fixed with 4% formaldehyde/PBS for 10 min. The remaining cells were then stained with 0.5% crystal violet for 10 min. Finally, the plates were washed with tap water and allowed to dry before plaques of wells containing >5 and <50 plaques were counted. These numbers were used to calculate titers. The detection limit of the assay is 200 PFU per ml of sample.

Tested Compounds

Figure 2:
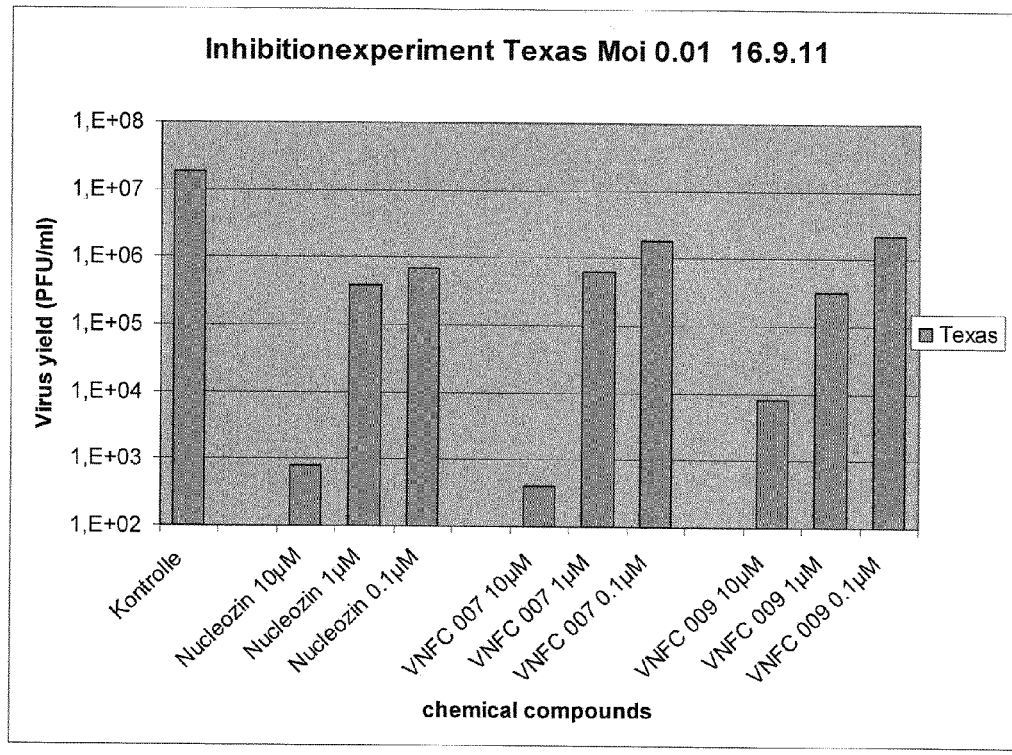
FIG. 2 is a bar chart diagram showing inhibition experiments performed on (A) Texas influenza virus, (B) H1N1 influenza virus.
Figure 2:
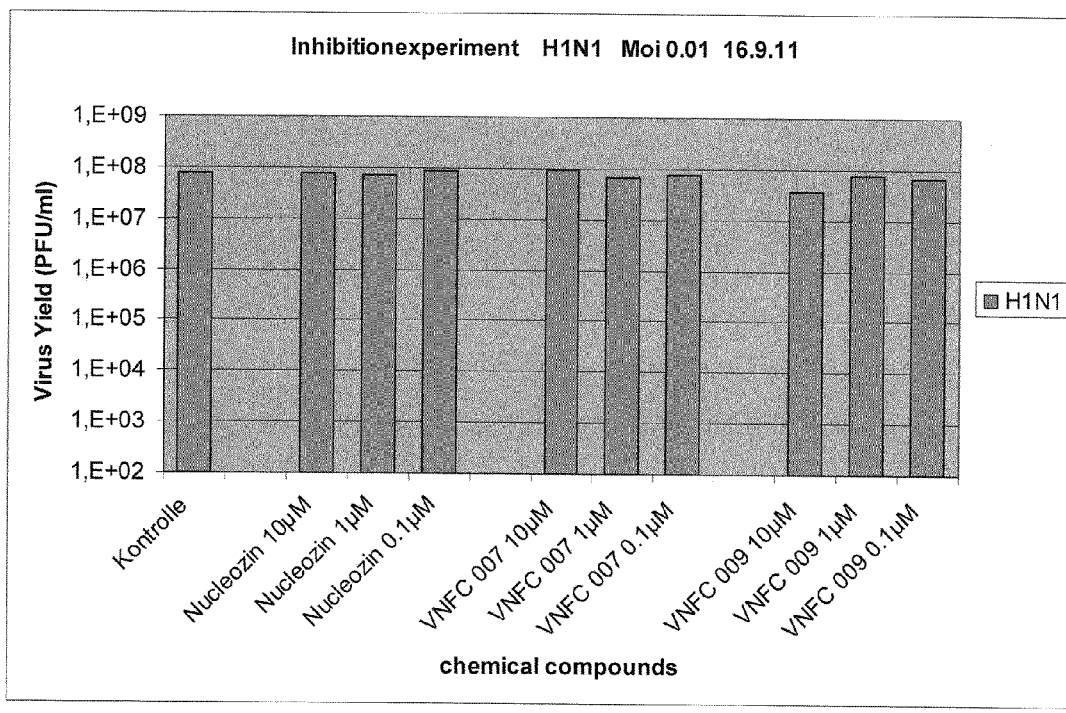

Compounds were dissolved in dimethyl sulfoxide (DMSO) to obtain 20 mM stock solutions which were stored at room temperature until use. Immediately before use, the stock solutions were diluted in DMEM medium containing 0.1% BSA. Dilutions of 20 mM DMSO without compounds served as negative controls. The compounds that were tested (cf. Table 1) were the inventive compounds prepared in Examples 1 and 2, i.e. (4-(2-chloro-4-nitrophenyl)piperazin-1-yl)(5-methyl-3-phenylisoxazol-4-yl)methanethione (termed VNFC 009) and (5-methyl-3-phenylisoxazol-4-yl)(4-(4-(trifluoromethyl)phenyl)piperazin-1-yl)methanethione (termed VNFC 0015), respectively. For comparison purposes, also (4-(2-chloro-4-nitrophenyl)piperazin-1-yl)(5-methyl-3-phenylisoxazol-4-yl)methanethione (termed VNFC 007) and (5-methyl-3-phenylisoxazol-4-yl)(4-(4-(trifluoromethyl)phenyl)piperazin-1-yl)methanone (termed VNFC 0014) were prepared and tested. Commercially available nucleozin was used as a reference. The results are shown in FIGS. 1 and 2.

TABLE 1

Tested compounds

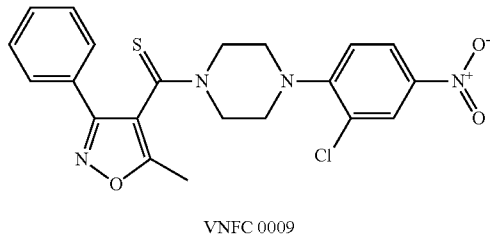

VNFC 0009

Nucleozin/VNFC 0007*

TABLE 1-continued

Tested compounds

VNFC 0015

VNFC 0014*

*not according to invention

From the test results it appears that the compounds of the invention are effective as viral inhibitors, in particular for influenza viruses.

Furthermore the antiviral activity against influenza virus of the compounds prepared in Example 6 (not according to the invention) and 7 (inventive compounds) have been tested in a virus assay as described herein above. The results are summarized in Table 2, wherein the compounds are referred to by the terms as identified in said Examples.

TABLE 2

| Compound | Antiviral activity Texas H1N1 |
|---|---|
| VNFC040* | +++ |
| VNFC041 | +++ |
| VNFC050* | +++ |
| VNFC051 | +++ |
| VNFC044* | +++ |
| VNFC045 | +++ |
| VNFC025* | ++ |
| VNFC026 | ++ |
| VNFC042* | − |
| VNFC043 | − |
| VNFC027* | + |
| VNFC028 | − |
| VNFC047* | ++ |
| VNFC046 | + |

*Not according to the invention

Caco2 Permeability Assay

A Caco2 permeability assay was performed using the inventive compound VNFC 0009 as well as Nucleozin. The assay showed good bioavailability of VNFC 0009 compared to Nucleozin: the Caco2 permeability in the apical to basal direction was about 30% higher than that of Nucleozin, and at the same time, the basal to apical Caco2 permeability of VNFC 0009 was nearly 7 times lower than that of Nucleozin.

The invention claimed is:
1. A compound of formula (I)

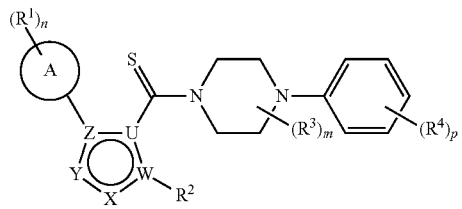

wherein
the ring A

is 6-membered aryl;
n is an integer of from 0 to 3;
m is an integer of from 0 to 2;
p is an integer of from 0 to 3;
each $R^1$ is independently selected from the group consisting of C1-C6 alkyl; C1-C6 alkoxy; OH; halogen; and $R^5R^6N$;
$R^2$ is selected from H and C1-C6 alkyl;
each $R^3$ is independently selected from C1-C6 alkyl;
each $R^4$ is independently selected from $NO_2$; halogen; C1-C6 alkyl and C1-C6 alkoxy;
$R^5$ and $R^6$ are independently selected from H and C1-C6 alkyl;
wherein any alkyl is optionally substituted with one or several halogen atoms; and
the ring of formula (III)

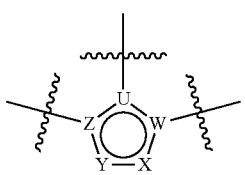

is a ring of formula (IIIa), (IIIb), (IIIc), (IIId), or (IIIe):

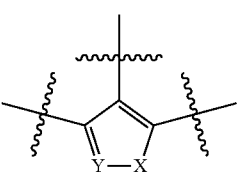

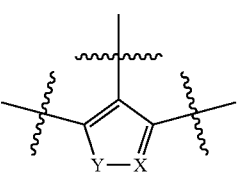

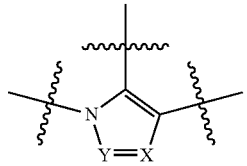

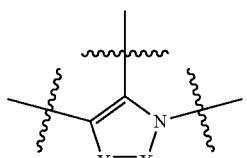

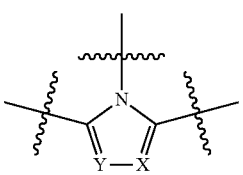

wherein
in formula (IIIa), X is NH or O, and Y is N or CH,
in formula (IIIb), X is N or CH, and Y is NH or O,
in formula (IIIc), X is N, and Y is N or CH,
in formula (IIId), X is N or CH, and Y is N or CH, and
in formula (IIIe), X is N or CH, and Y is N or CH,
or a pharmaceutically acceptable salt thereof.

2. The compound according to claim 1,
wherein
each $R^1$ is independently selected from C1-C6 alkyl; OH; halogen; and $R^5R^6N$;
$R^2$ is selected from H and C1-C6 alkyl;
each $R^3$ is independently selected from C1-C6 alkyl;
each $R^4$ is independently selected from $NO_2$; halogen; and C1-C6 alkyl;
each $R^5$ and $R^6$ is independently selected from H and C1-C6 alkyl;
wherein any alkyl is optionally substituted with one or several halogen atoms;
or a pharmaceutically acceptable salt thereof.

3. The compound according to claim 1, wherein any C1-C6 alkyl moiety is selected from C1-C3 alkyl;
or a pharmaceutically acceptable salt thereof.

4. The compound according to claim 3, wherein any C1-C6 alkyl moiety is methyl;
or a pharmaceutically acceptable salt thereof.

5. The compound according to claim 1, wherein n is 0,
or a pharmaceutically acceptable salt thereof.

6. The compound according to claim 1, wherein m is 0,
or a pharmaceutically acceptable salt thereof.

7. The compound according to claim 1, wherein the ring of formula (III) is a ring of formula (IIIc), (IIIb), (IIIc), or (IIId),
or a pharmaceutically acceptable salt thereof.

8. The compound according to claim 1, wherein Y is N,
or a pharmaceutically acceptable salt thereof.

9. The compound according to claim 1, wherein Y is NH,
or a pharmaceutically acceptable salt thereof.

10. The compound according to claim 1, wherein Y is O,
or a pharmaceutically acceptable salt thereof.

11. The compound according to claim 1, wherein X is N,
or a pharmaceutically acceptable salt thereof.

12. The compound according to claim 1, wherein X is NH,
or a pharmaceutically acceptable salt thereof.

13. The compound according to claim 1, wherein X is O, or a pharmaceutically acceptable salt thereof.

14. The compound according to claim 1, wherein the ring of formula (III) is a ring of formula (IIId), or a pharmaceutically acceptable salt thereof.

15. The compound according to claim 1, wherein the ring of formula (III) is a ring of formula (IIIa), (IIIb), (IIIc), or (IIIe), or a pharmaceutically acceptable salt thereof.

16. The compound according to claim 1, wherein the ring of formula (III) is a ring of formula (IIIc), or a pharmaceutically acceptable salt thereof.

17. The compound according to claim 1, wherein the ring of formula (III) is a ring of formula (IIIa), (IIIb), (IIId), or (IIIe), or a pharmaceutically acceptable salt thereof.

18. The compound according to claim 1, wherein the ring A is phenyl, or a pharmaceutically acceptable salt thereof.

19. A pharmaceutical composition comprising a compound according to claim 1, or a pharmaceutically acceptable salt thereof, and at least one pharmaceutically acceptable excipient.

20. A method of preparing a compound of formula (I)

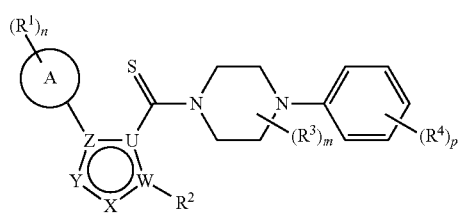

wherein the ring A

is 6-membered aryl or heteroaryl;
n is an integer of from 0 to 3;
m is an integer of from 0 to 2;
p is an integer of from 0 to 3;
each $R^1$ is independently selected from the group consisting of C1-C6 alkyl; C1-C6 alkoxy; OH; halogen; and $R^5R^6N$;
$R^2$ is selected from H and C1-C6 alkyl;
each $R^3$ is independently selected from C1-C6 alkyl;
each $R^4$ is independently selected from $NO_2$; halogen; C1-C6 alkyl and C1-C6 alkoxy;
$R^5$ and $R^6$ are independently selected from H and C1-C6 alkyl;
wherein any alkyl is optionally substituted with one or several halogen atoms;

the ring of formula (III)

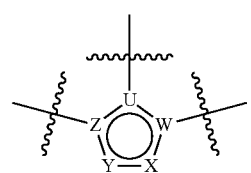

is a ring of formula (IIIa), (IIIb), (IIIc), (IIId), or (IIIe)

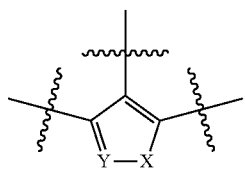

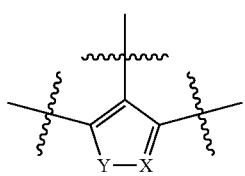

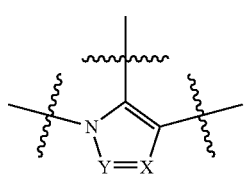

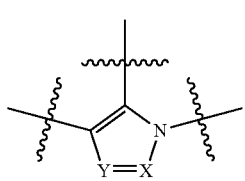

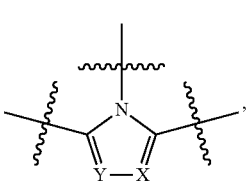

wherein
in formula (IIIa), X is NH or O, and Y is N or CH,
in formula (IIIb), X is N or CH, and Y is NH or O,
in formula (IIIc), X is N, and Y is N or CH,
in formula (IIId), X is N or CH, and Y is N or CH, and
in formula (IIIe), X is N or CH, and Y is N or CH:
or a pharmaceutically acceptable salt thereof,
comprising reacting a compound of formula (II)

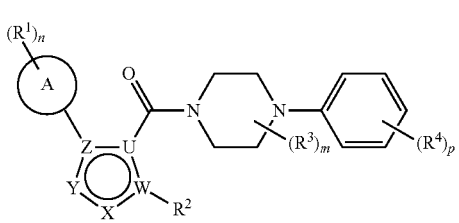

wherein the ring A, n, m, p, $R^1$, $R^2$, $R^3$, $R^4$ and the ring of formula (III):

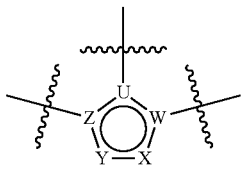
(III)

are as defined herein above,
with $P_2S_5 \cdot 2\, C_5H_5N$ as a thionating agent in a liquid solvent medium.

21. A method of treatment of a viral infection comprising administering to a vertebrate patient in need thereof a therapeutically effective amount of a compound according to claim 1, or a pharmaceutically acceptable salt thereof.

22. The method according to claim 21, wherein the viral infection is influenza.

23. The compound according to claim 1, wherein the ring of formula (III) is a ring of formula (IIIa), or a pharmaceutically acceptable salt thereof.

24. The compound according to claim 23, wherein Y is N, or a pharmaceutically acceptable salt thereof.

25. The compound according to claim 24, wherein X is O, or a pharmaceutically acceptable salt thereof.

26. The compound according to claim 14, wherein X is N, or a pharmaceutically acceptable salt thereof.

27. The compound according to claim 26, wherein Y is N, or a pharmaceutically acceptable salt thereof.

28. The compound according to claim 16, wherein Y is N, or a pharmaceutically acceptable salt thereof.

29. The compound according to claim 1, selected from the group consisting of:

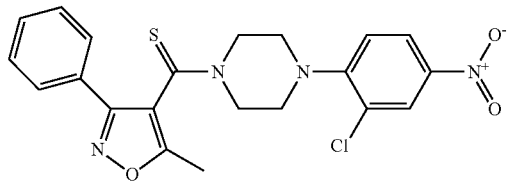 [SMILES: Cc1onc(-c2ccccc2)c1C(=S)N1CCN(c2ccc([N+](=O)[O-])cc2Cl)CC1]

(4-(2-chloro-4-nitrophenyl)piperazin-1-yl) (5-methyl-3-phenylisoxazol-4-yl)methanethione;

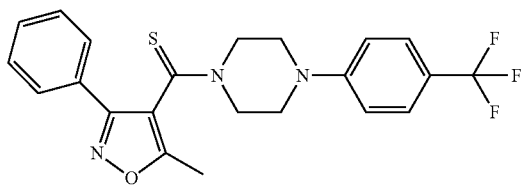

(5-methyl-3-phenylisoxazol-4-yl) (4-(4-(trifluoromethyl)phenyl) piperazin-1-yl) methanethione;

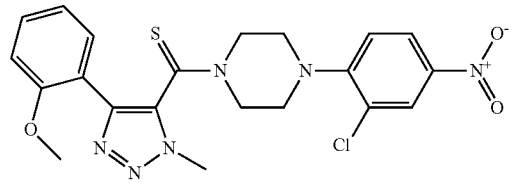

(4-(2-chloro-4-nitrophenyl) piperazin-1-yl) (4-(2-methoxyphenyl)-1-methyl-1H-1,2,3-triazol-5-yl)methanethione;

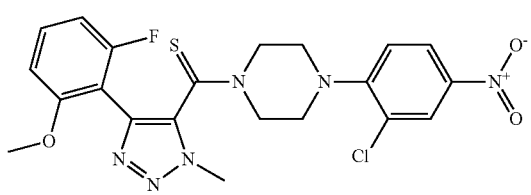 [SMILES: COc1cccc(F)c1-c1nnn(C)c1C(=S)N1CCN(c2ccc([N+](=O)[O-])cc2Cl)CC1]

(4-(2-chloro-4-nitrophenyl)piperazin-1-yl) (4-(2-fluoro-6-methoxyphenyl)-1-methyl-1H-1,2,3-triazol-5-yl) methanethione;

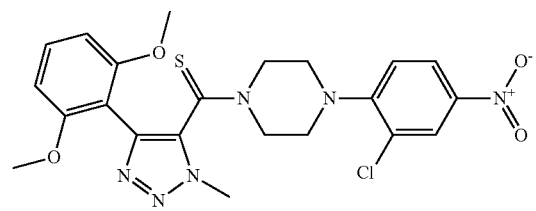 [SMILES: COc1cccc(OC)c1-c1nnn(C)c1C(=S)N1CCN(c2ccc([N+](=O)[O-])cc2Cl)CC1]

(4-(2-chloro-4-nitrophenyl)piperazin-1-yl) (4-(2,6-dimethoxyphenyl)-1-methyl-1H-1,2,3-triazol-5-yl) methanethione;

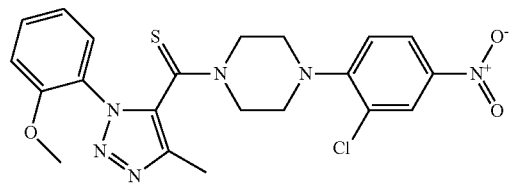 [SMILES: COc1ccccc1-n1nnc(C)c1C(=S)N1CCN(c2ccc([N+](=O)[O-])cc2Cl)CC1]

(4-(2-chloro-4-nitrophenyl)piperazin-1-yl) (1-(2-methoxyphenyl)-4-methyl-1H-1,2,3-triazol-5-yl)methanethione;

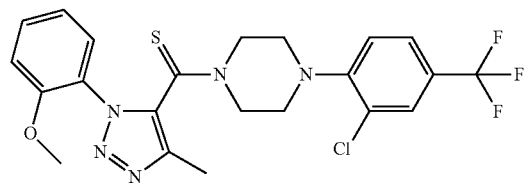 [SMILES: COc1ccccc1-n1nnc(C)c1C(=S)N1CCN(c2ccc(C(F)(F)F)cc2Cl)CC1]

(4-(2-chloro-4-(trifluoromethyl)phenyl)piperazin-1-yl) (1-(2-methoxyphenyl)-4-methyl-1H-1,2,3-triazol-5-yl) methanethione;

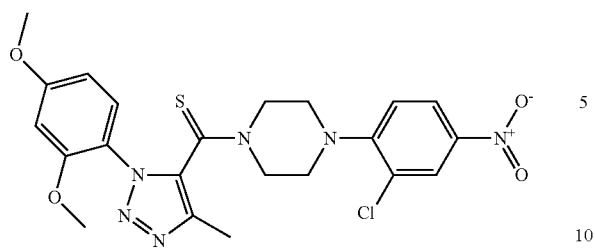
(4-(2-chloro-4-nitrophenyl)piperazin-1-yl) (1-(2,4-dimethoxyphenyl)-4-methyl-1H-1,2,3-triazol-5-yl)methanethione;
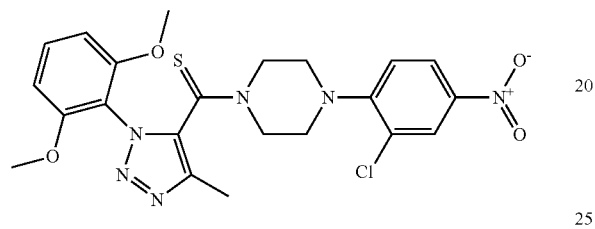
(4-(2-chloro-4-nitrophenyl)piperazin-1-yl) (1-(2,6-dimethoxyphenyl)-4-methyl-1H-1,2,3-triazol-5-yl)methanethione;
and pharmaceutically acceptable salts thereof.
* * * * *